US008026217B2

(12) United States Patent
Dawson-Scully et al.

(10) Patent No.: US 8,026,217 B2
(45) Date of Patent: Sep. 27, 2011

(54) COMPOSITIONS AND METHODS FOR TREATING NEURAL ANOXIA AND SPREADING DEPRESSION

(75) Inventors: Ken Dawson-Scully, Boca Raton, FL (US); R. Meldrum Robertson, Napanee (CA); Gary A. B. Armstrong, Toronto (CA); Marla Sokolowski, Toronto (CA)

(73) Assignee: Florida Atlantic University, Boca Raton, FL (US)

( * ) Notice: Subject to any disclaimer, the term of this patent is extended or adjusted under 35 U.S.C. 154(b) by 0 days.

(21) Appl. No.: 12/245,427

(22) Filed: Oct. 3, 2008

(65) Prior Publication Data

US 2009/0124558 A1    May 14, 2009

Related U.S. Application Data

(60) Provisional application No. 60/977,321, filed on Oct. 3, 2007, provisional application No. 61/055,855, filed on May 23, 2008.

(51) Int. Cl.
*A61K 38/00* (2006.01)
*A61K 31/50* (2006.01)
*A61K 31/495* (2006.01)
*A61P 25/02* (2006.01)
*A61P 23/00* (2006.01)
*A01N 43/58* (2006.01)
*A01N 43/60* (2006.01)

(52) U.S. Cl. .............. 514/18.2; 514/18.3; 514/250

(58) Field of Classification Search .............. None
See application file for complete search history.

(56) References Cited

U.S. PATENT DOCUMENTS

| | | | |
|---|---|---|---|
| 5,990,177 A | 11/1999 | Brown | |
| 6,300,327 B1 * | 10/2001 | Knusel et al. | 514/211.08 |
| 6,391,869 B1 * | 5/2002 | Parks et al. | 514/211.07 |
| 2004/0087539 A1 | 5/2004 | Du | |
| 2005/0170345 A1 | 8/2005 | Sun et al. | |
| 2007/0184044 A1 | 8/2007 | Dawson-Scully et al. | |

OTHER PUBLICATIONS

Baumner et al. Effects of inhibitors of cGMP-dependent protein kinase in atrial heart and aortic smooth muscle from rats. European Journal of Pharmacology. 1995. vol. 273, pp. 295-298.*
Taylor et al. Inhibition of cGMP-Dependent Protein Kinase by the Cell-Permeable Peptide DT-2 Reveals a Novel Mechanism of Vasoregulation. Molecular Pharmacology. 2004, vol. 65, Nol. 5, pp. 1111-1119.*
Iadecola. From CSD to headache: A long and winding road. Nature Medicine, 2002. vol. 8, No. 2., pp. 110-112.*
Dawson-Scully et al., Natural Variation in the Thermotolerance of Neural Function and Behavior due to a cGMP-Dependent Protein Kinase, PloS ONE, 2007, vol. 2(8), pp. 1-9, published on-line Aug. 22, 2007.
Tomoki et al., Phosphodiesterase inhibitors are neuroprotective to cultured spinal motor neurons, J. of Neuroscience Research, 2003, 71(4): 485-495 (Abstract Only).
Wu et al., Protective effects of brain-derived neurotrophic factor against neurotoxicity of 3-nitropropionic acid in rat cortical neurons, J. of Neuroscience Research, 2009 (Abstract only).
Smith et al., Physiological studies of cortical spreading depression, Biol. Rev., 2006, 81, pp. 457-481.
Somjen, Ion Regulation in the Brain: Implications for Pathophysiology, The Neuroscientist, 2002, 8(3), 254-267.
Somjen, Mechanisms of Spreading Depression and Hypoxic Spreading Depression-Like Depolarization, Physiological Review, Jul. 2001, 81(3), 1065-1096.
Culmsee et al., Nitric Oxide Donors Induce Neurotrophin-Like Survival Signaling and Protect Neurons against Apoptosis, Molecular Pharmacology, 2005, 68(4), 1006-1017.
Dawson-Scully et al. Controlling Anoxic Tolerance in Adult Drosophila via The cGMP-PKG Pathway;The Journal of Experimental Biology 213, 2410-2416; Pub. 2010.
Kruuse et al., Migrane Can Be Induced By Sildenafil Without Changes in Middle Cerebral Artery Diameter; DOI: 10,1093/brain/awg009; Brain (2003). 126, 241-247.

* cited by examiner

*Primary Examiner* — Marcela M Cordero Garcia
(74) *Attorney, Agent, or Firm* — Gregory A. Nelson; Amy Dobbelsere; Novak Druce + Quigg LLP

(57) ABSTRACT

Compositions and methods for protecting neural tissue (e.g., neurons) from anoxia and spreading depression (SD) involve inhibiting the cGMP-dependent protein kinase (PKG) pathway. It was discovered that the PKG pathway plays a crucial role in regulating SD and tolerance to anoxia in the central nervous system (CNS). Inhibition of the PKG pathway greatly reduces SD and increases tolerance to anoxia (i.e., hypoxia), while activation of the pathway exacerbates SD pathology. The compositions and methods can be used to treat any condition associated with SD or anoxia, including stroke, spinal cord injury, neurogenerative disease, dizziness, headaches, and migraines.

6 Claims, 15 Drawing Sheets

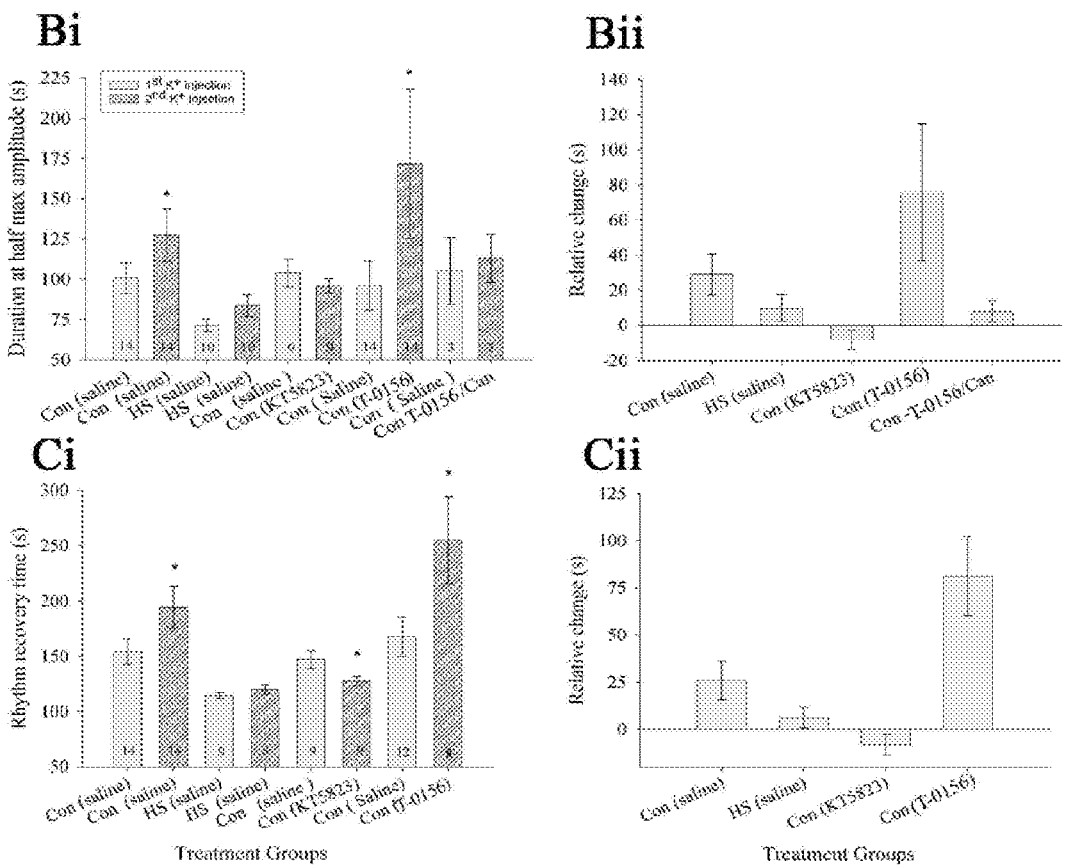
FIGURE 1B-C

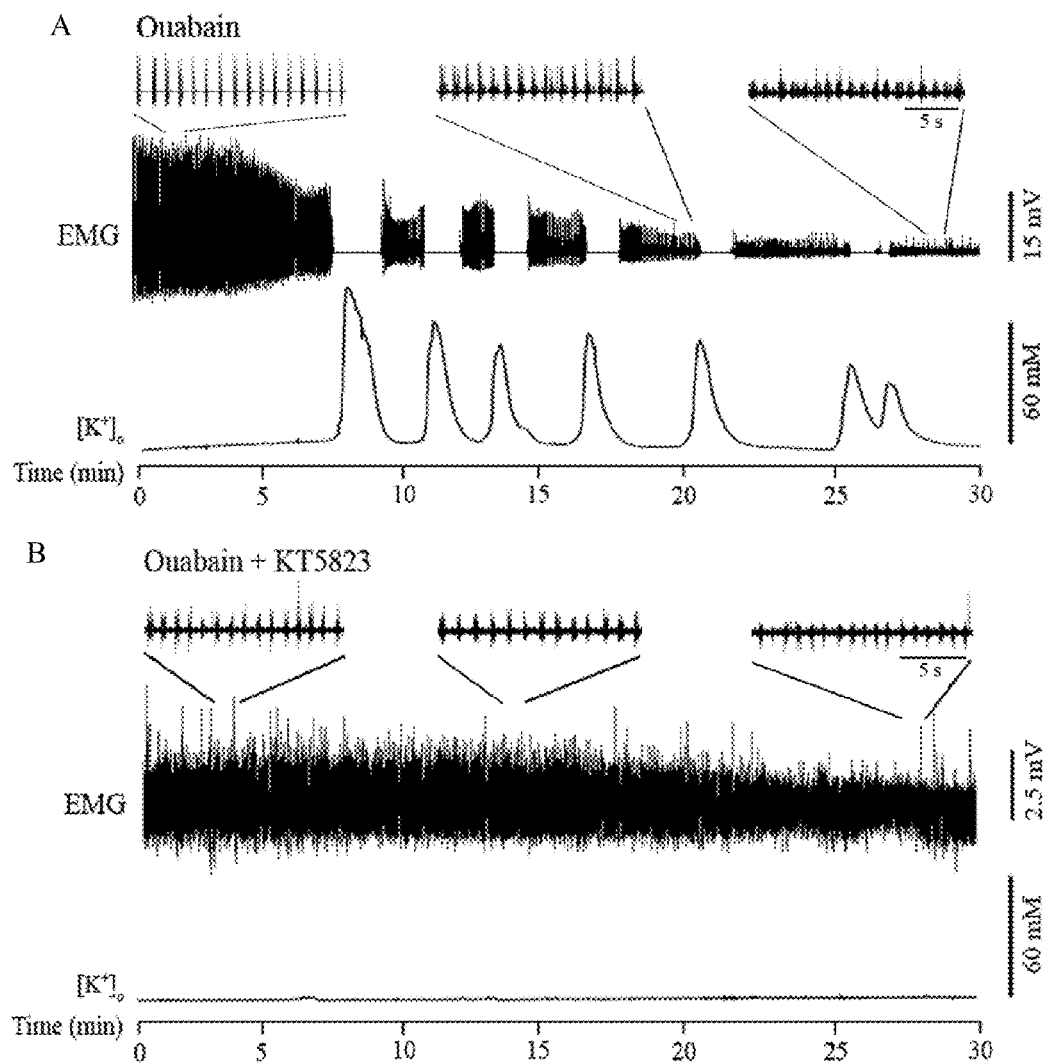
FIGURE 2A-B

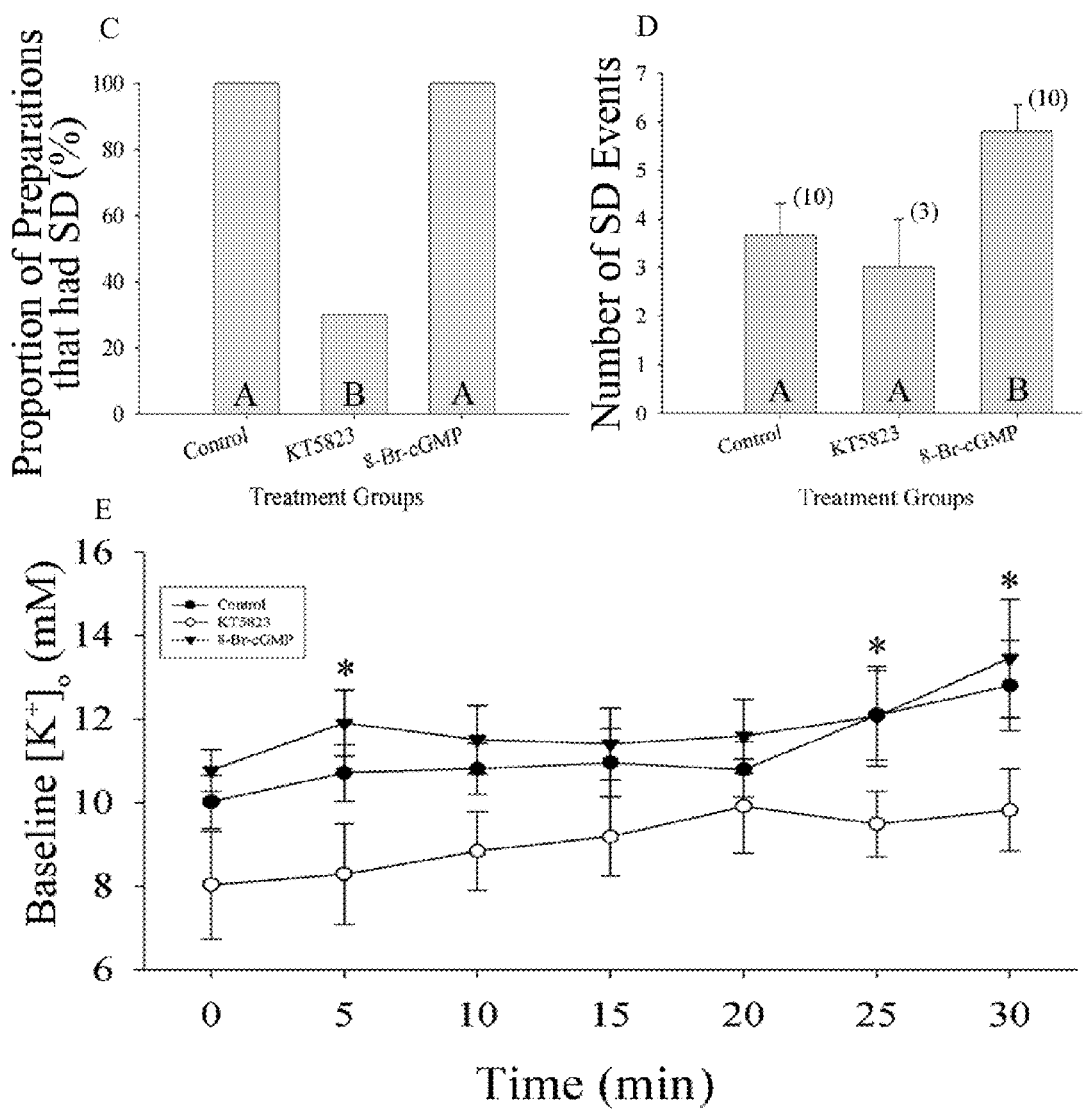
FIGURE 2C-E

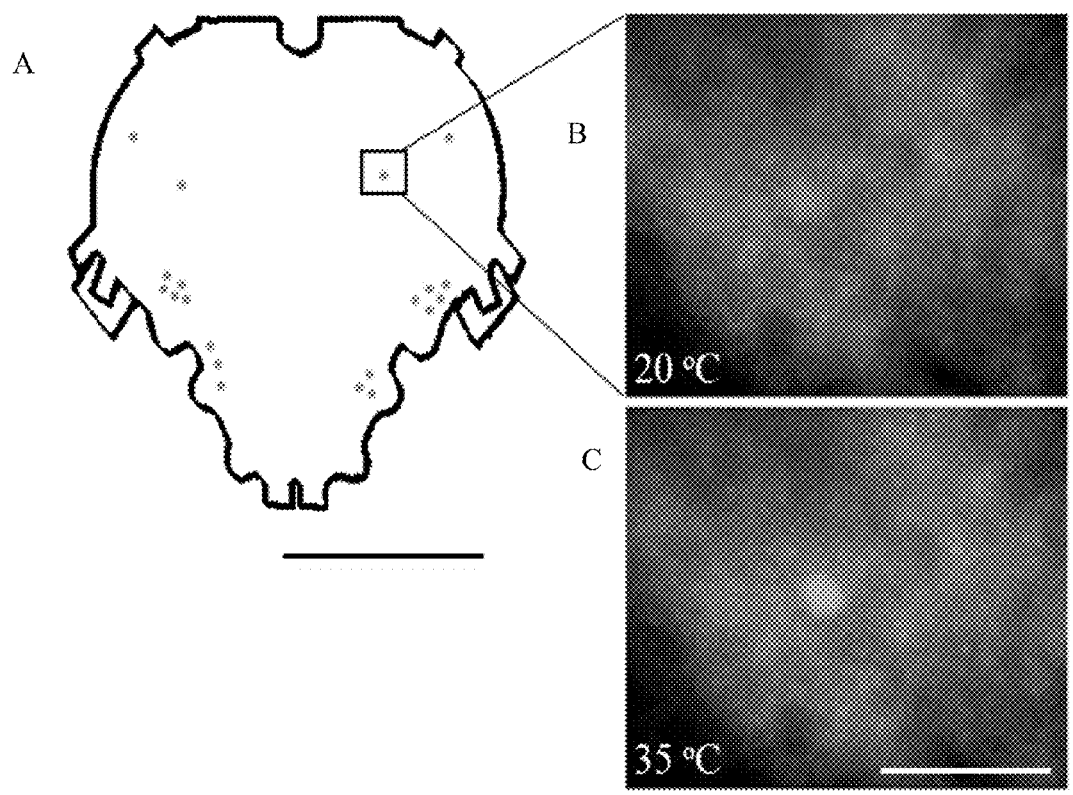
FIGURE 4A-C

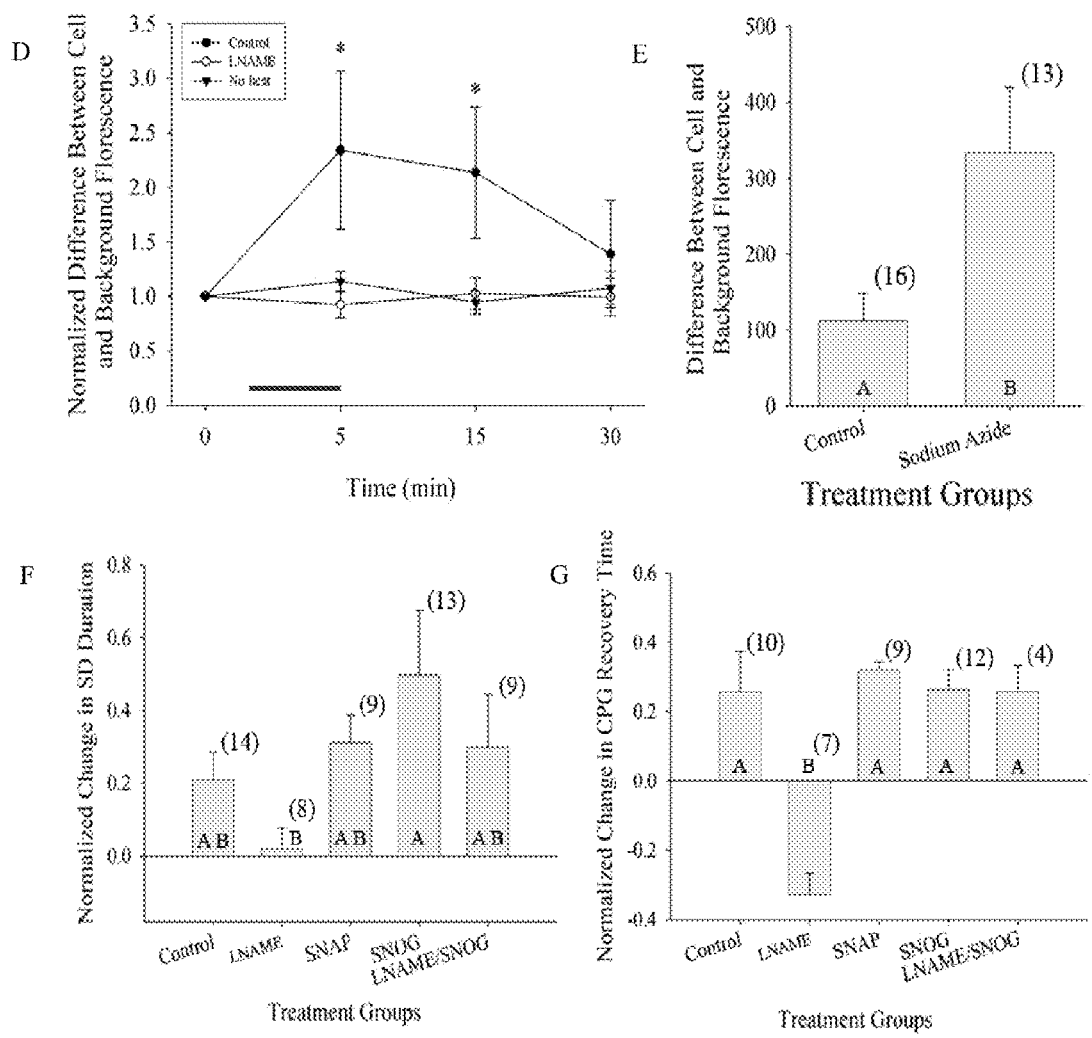
FIGURE 4D-G

SEQUENCE LISTING

<160> NUMBER OF SEQ ID NOS: 6

<210> SEQ ID NO 1
<211> LENGTH: 24
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 1

Arg Gln Ile Lys Ile Trp Phe Gln Asn Arg Arg Met Lys Trp Lys Lys
1               5                   10                  15

Leu Arg Lys Lys Lys Lys Lys His
            20

<210> SEQ ID NO 2
<211> LENGTH: 21
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 2

Tyr Gly Arg Lys Lys Arg Arg Gln Arg Arg Pro Pro Leu Arg Lys
1               5                   10                  15

Lys Lys Lys Lys His
            20

<210> SEQ ID NO 3
<211> LENGTH: 13
<212> TYPE: PRT
<213> ORGANISM: Human immunodeficiency virus type 1

<400> SEQUENCE: 3

Tyr Gly Arg Lys Lys Arg Arg Gln Arg Arg Pro Pro
1               5                   10

<210> SEQ ID NO 4
<211> LENGTH: 8
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 4

Leu Arg Lys Lys Lys Lys Lys His
1               5

<210> SEQ ID NO 5
<211> LENGTH: 7
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 5

Arg Lys Arg Ala Arg Lys Glu
1               5

<210> SEQ ID NO 6
<211> LENGTH: 7
<212> TYPE: PRT

```
<213> ORGANISM: ARTIFICIAL SEQUENCE
<220> FEATURE:
<223> OTHER INFORMATION: SYNTHETIC CONSTRUCT

<400> SEQUENCE: 6

Arg Lys Arg Ser Arg Ala Glu
1               5
```

COMPOSITIONS AND METHODS FOR TREATING NEURAL ANOXIA AND SPREADING DEPRESSION

CROSS-REFERENCE TO RELATED APPLICATIONS

The present application claims the priority of U.S. provisional application No. 60/977,321 filed on Oct. 3, 2007 and U.S. provisional application No. 61/055,855 filed on May 23, 2008.

FIELD OF THE INVENTION

The present invention relates to compositions and methods for protecting neural tissue from anoxia and/or spreading depression. The present invention further relates to compositions and methods for mitigating side effects associated with pharmaceuticals that manipulate the nitric oxide/cyclic guanosine monophosphate pathway.

BACKGROUND $K^+$ channels are structurally and functionally diverse families of $K^+$-selective channel proteins which are ubiquitous in cells, indicating their central importance in regulating a number of key cell functions. $K^+$ channels are important regulators of numerous biological processes, including secretory processes, muscle contraction, and post-ischemia cardioprotection. Electrophysiological studies have disclosed the existence of $K^+$ channels in nearly all cell types.

Spreading depression is an abrupt rise in extracellular potassium ($[K^+]_o$) and depression of electrical activity in nervous tissue; it shares many characteristics of cortical spreading depression (CSD) (Leão, A. A. P., J. Neurophysiol. 7:359-390, 1944). In mammalian tissue, CSD has been associated with several important pathologies including stroke, seizures and migraine (Smith et al., Biol. Rev. Camb. Philos. Soc. 81:457-481, 2006; Somjen, G. G., Neuroscientist 8:254-267, 2002; Somjen, G. G., Physiol. Rev. 81:1065-1096, 2001). CSD is increasingly accepted as a primary causative agent for migraine, particularly migraine with aura.

SUMMARY

Based on the discovery that $K^+$ channel activity may be involved in protection of neural tissue from anoxia (also referred to herein as "hypoxia"), compositions and methods for protecting neural tissue (e.g., neurons) from anoxia involving inhibition of the cGMP-dependent protein kinase (PKG) pathway are described herein. In a locusts model system in which the animals are subjected to a rapid rise in extracellular $K^+$ and anoxia, treatment with a PKG pathway inhibitor significantly reduced the length of the term of SD induced by the extracellular $K^+$ and increased the animals' tolerance to acute hypoxic conditions.

Described herein are pharmaceutical compositions including a pharmacological inhibitor of the PKG pathway in an amount effective for treating or preventing one or both of neural anoxia and spreading depression, and an excipient.

Also described herein are pharmaceutical compositions each including a composition for treating erectile dysfunction or angina; a PKG pathway pharmacological inhibitor in an amount effective for treating or preventing one or both of neural anoxia and spreading depression; and an excipient. The PKG pathway pharmacological inhibitor can be a PKG inhibitor, a sGC inhibitor, a cGMP-specific antagonist, or a protein phosphatase inhibitor (e.g., Okadaic acid, Microcystin, Calyculin, and Cantharidin). Examples of PKG pathway pharmacological inhibitors include KT5823; H-9 dihydrochloride; (Rp)-8bromo-PET-cyclic GMPS; (Rp)-8-pCPT-cyclic GMPS,TEA; Rp-8-Br-cGMPS, Na; DT-3; DT-2; an amino acid having a sequence RKRARKE (SEQ ID NO:5), 4H-8-Bromo-1,2,4-oxadiazolo(3,4-d) benz(b)(1,4)oxazin-1-one; 1H-[1,2,4]Oxadiazolo[4,3-a]quinoxalin-1-one (ODQ); and 6-Anilino-5,8-quinolinequinone. The pharmacological inhibitor typically inhibits $K^+$ ion channel function. The composition for treating erectile dysfunction or angina can be a phosphodiesterase type 5 inhibitor (e.g., sildenafil, tadalafil, and vardenafil), nitroglycerine, pentaerythritol tetranitrate, sodium nitroprusside, isosorbide mononitrate, or a isosorbide dinitrate.

In another embodiment, a method includes administering a therapeutically effective amount of a PKG pathway pharmacological inhibitor to a patient having a medical condition such as neuronal damage from spinal cord injury, neuronal damage from stroke, neural anoxia, spreading depression, migraine, and a predisposition in the patient to spreading depression events. The PKG pathway pharmacological inhibitor can be a PKG inhibitor, a cGMP-specific antagonist, an inhibitor of $K^+$ ion channel function, a protein phosphatase inhibitor, and a sGC inhibitor. Examples of PKG pathway pharmacological inhibitors include KT5823; (Rp)-8-bromo-PET-cyclic GMPS; (Rp)-8-pCPT-cyclic GMPS, TEA; Rp-8-Br-cGMPS,Na; DT-3; DT-2; an amino acid having a sequence RKRARKE (SEQ ID NO: 5); Okadaic acid; Microcystin; Calyculin; Cantharidin; 4H-8-Bromo-1,2,4-oxadiazolo(3,4-d)benz(b)(1,4)oxazin-1-one; 1H-[1,2,4]Oxadiazolo[4,3-a]quinoxalin-1-one (ODQ); and 6-Anilino-5,8-quinolinequinone. Administration of the PKG pathway pharmacological inhibitor mitigates or prevents neural death and damage in the patient.

In another embodiment, a method includes administering a therapeutically effective amount of a PKG pathway pharmacological inhibitor for mitigating at least one side effect associated with a pharmaceutical composition that modulates a nitric oxide/cyclic guanosine monophosphate pathway to a patient being treated for erectile dysfunction or angina. The pharmaceutical composition typically treats erectile dysfunction or angina. Administration of the PKG pathway pharmacological inhibitor mitigates or prevents spreading depression events in the patient. The at least one side effect can include headache, dizziness, abnormal vision, and migraine. The PKG pathway pharmacological inhibitor can be a PKG inhibitor. Examples of pharmaceutical compositions that modulate a nitric oxide/cyclic guanosine monophosphate pathway include phosphodiesterase type 5 inhibitor, nitroglycerine, pentaerythritol tetranitrate, sodium nitroprusside, isosorbide mononitrate, and isosorbide dinitrate. Examples of phosphodiesterase type 5 inhibitors include sildenafil, tadalafil and vardenafil. In some embodiments, the PKG pathway pharmacological inhibitor is administered to the patient in combination with a pharmaceutical composition that modulates a nitric oxide/cyclic guanosine monophosphate pathway.

In yet another embodiment, described herein is the use of a pharmacological inhibitor of the PKG pathway for providing protection from neural anoxia and/or spreading depression.

In another embodiment, described herein is use of an effective amount of a pharmacological inhibitor of the PKG pathway for mitigating the side effects in a patient of a pharmaceutical composition that manipulates the nitric oxide/cyclic guanosine monophosphate pathway.

Unless otherwise defined, all technical terms used herein have the same meaning as commonly understood by one of ordinary skill in the art to which this invention belongs.

By the term "spreading depression" is meant an abrupt rise in extracellular potassium ($[K^+]_o$) and depression of electrical activity in nervous tissue.

As used herein, "treatment" and "treating" are intended to refer to inhibiting, eliminating, ameliorating, diminishing and/or reducing cellular damage and/or symptoms associated with a disease or condition, e.g. spreading depression and/or neural anoxia. "Treating" includes, but is not limited to, reducing the precursor symptoms of neural failure, such as disturbances in breathing patterns. Compositions as described herein may also or alternatively be a prophylactic, i.e., used to partially or completely prevent a disease or condition or symptom thereof.

By "neural anoxia protection" is meant lowering the level of oxygen at which neural function becomes abnormal and/or increasing the time before neural function becomes abnormal when subject to anoxia.

As used herein, the term "neural tissue" means cells (e.g., neurons) within the central nervous system (CNS) (e.g., brain, spinal cord).

Where the terms "patient" and "subject" are used interchangeably in the present specification, they include animals. In one embodiment, the patient is a mammal, and in a preferred embodiment, the patient is human.

As used herein, "an effective amount" or "a therapeutically effective" amount is intended to refer to the total amount of the active compound of the method that is sufficient to show a meaningful patient benefit. This term is also intended to refer to an amount that returns to normal, either partially or completely, physiological or biochemical parameters associated with induced cellular damage.

As used herein "mitigation" or "mitigating" of side effects includes, without limitation, any of reducing the incidence, intensity, severity or duration of side effects.

Although compositions and methods similar or equivalent to those described herein can be used in the practice or testing of the present invention, suitable compositions and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 1B is a pair of graphs illustrating the effects of drug treatments KT5823 (PKG inhibitor, Calbiochem (EMD) Sciences, San Diego, Calif., catalogue #420321) and T-0156 (PDE 5/6 inhibitor) on SD-like events in the metathoracic ganglion of locusts injected with high potassium into the metathoracic ganglion. A first high potassium injection was used as a control and a second high potassium injection was administered after drug treatment. (Bi) illustrates the severity of SD-like events as characterized by duration at half the maximum amplitude. (Bii) illustrates the percentage difference in SD duration (second injection relative to first injection).

FIG. 1C is a pair of graphs illustrating the effects of drug treatments KT5823 and T-0156 on SD-like events in the metathoracic ganglion of locusts injected with high potassium into the metathoracic ganglion. Figure Ci illustrates the severity of SD as measured by the length of time to recover ventilatory pattern activity. Figure Cii illustrates the percentage difference in rhythm recovery time (second injection relative to first injection.)

FIG. 2A is a plot illustrating ventilatory motor activity (Ventilatory EMG) and extracellular potassium concentration in the metathoracic ganglion ($[K^+]_o$) of the locust in which repetitive SD was elicited by treatment with $10^{-4}$M ouabain ($Na^+/K^+$ ATPase antagonist) in control and 8-Br-cGMP-treated (PKG activator) animals.

FIG. 2B is a plot illustrating eradication of repetitive SD by prior bath application of KT5823.

FIG. 2C is a graph illustrating a reduction by KT5823 in the percentage of animals showing repetitive SD in response to ouabain.

FIG. 2D is a graph illustrating that in animals that showed repetitive SD, control and KT5823-treated preparations had fewer repetitive SD events than 8-Br-cGMP-treated animals. Error bars are ±SEM. Numbers in brackets represent sample sizes.

FIG. 2E is a graph illustrating the reduction in the baseline $[K^+]_o$ levels during ouabain exposure for animals pretreated with KT5823.

FIG. 4A is a schematic diagram of the locust metathoracic ganglion stained with diaminofluorescein-2-diacetate (DAF2-DA) to reveal NO-producing cells.

FIG. 4B is an image of a fluorescing cell body from the locust metathoracic ganglion stained with DAF2-DA at room temperature (20° C.). Letter in histogram bars represent statistical groupings using a post-hoc test, whereby bars with different letters are significantly different (Tukey, p<0.05).

FIG. 4C is an image of a fluorescing cell body from the locust metathoracic ganglion stained with DAF2-DA immediately following exposure to heat (35° C.).

FIG. 4D is a graph illustrating the quantification of the change in fluorescence of a fluorescing cell body from the locust metathoracic ganglion stained with DAF2-DA following exposure to heat (3 minutes at 35° C.); without exposure to heat and with exposure to heat and treatment with the NO synthase inhibitor N(G)-nitro-L-arginine methyl ester (LNAME).

FIG. 4E is a graph illustrating the difference in fluorescence of cell bodies from the locust metathoracic ganglion stained with DAF2-DA for control cell bodies and cell bodies subject to chemical anoxia via treatment with sodium azide. Error bars are ±SEM. Numbers in brackets represent sample sizes.

FIG. 4F is a graph illustrating is a diagram illustrating the SD duration of LNAME treated preparations, control preparations, preparations treated with the NO donors S-nitroso-N-acetyl-D-penicillamine (SNAP) and S-nitrosoglutathione (SNOG), and preparations co-treated with both LNAME and SNOG (LNAME/SNOG). Error bars are ±SEM. Numbers in brackets represent sample sizes.

FIG. 4G illustrates the recovery time following SD in LNAME treated preparations control preparations, preparations treated with the NO donors SNAP and SNOG, and preparations co-treated with both LNAME and SNOG (LNAME/SNOG). Error bars are ±SEM. Numbers in brackets represent sample sizes.

DETAILED DESCRIPTION

Figure 1A:
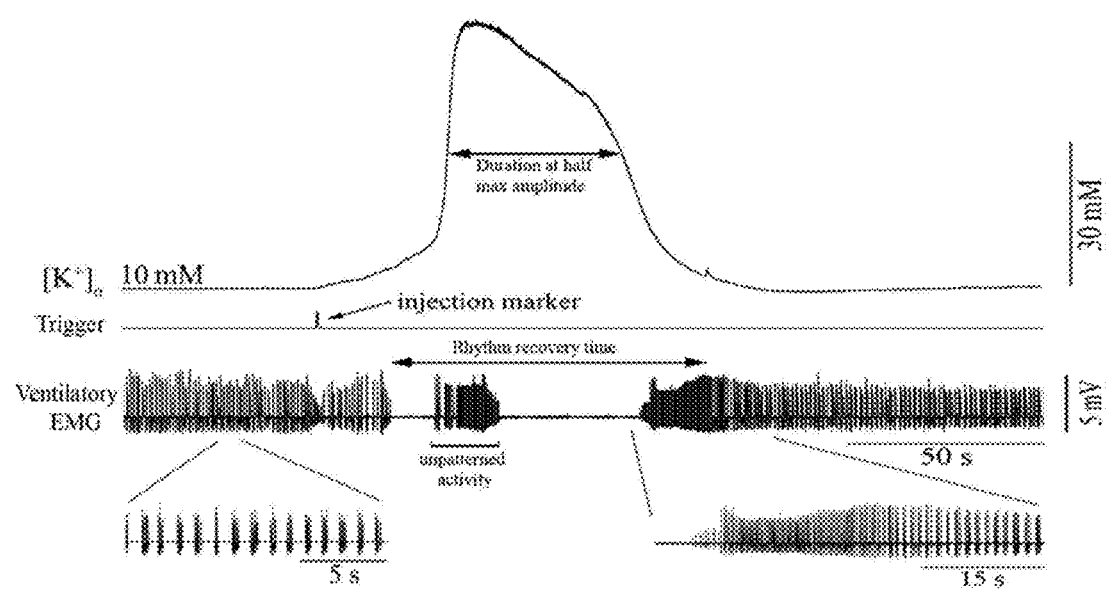
FIG. 1A is a plot illustrating that injection of saline containing elevated potassium evokes SD-like events in the metathoracic ganglion of semi-dissected locusts ("preparations") and upon restoration of the potassium ion gradient the neural activity recovers and the semi-dissected animals begin to ventilate again.

The invention encompasses compositions and methods for protecting neural tissue (e.g., neurons) from anoxia and SD that involve inhibiting the PKG pathway. It was discovered that the PKG pathway plays a crucial role in regulating SD and tolerance to anoxia in the CNS. Inhibition of the PKG pathway greatly reduces SD and increases tolerance to anoxia (i.e., hypoxia), while activation of the pathway with 8-Br-cGMP exacerbates SD pathology. Both genetic and pharmacological experiments described below demonstrate that there is a negative relationship between PKG activity and anoxic tolerance. The compositions and methods described herein can be used to treat any condition associated with SD or anoxia, including stroke, spinal cord injury, neurogenerative disease, dizziness, headaches, and migraines. For example, administering a composition including a PKG pathway inhibitor to a human would mitigate the underlying causes of migraine and headache as a side-effect of treatments, such as PDE5 inhibitors, for angina and erectile dysfunction. Further, by coupling the inhibition of the PKG pathway through the use of PKG or PP2A inhibitors directed specifically at the nervous system during use of a PDE5 inhibitor, the potential side effect of migraines could be mitigated before onset. As demonstrated in the Examples, the pathway providing anoxic and spreading depression protection is compromised by T-0156, a phosphodiesterase (PDE) inhibitor similar to Viagra™, Levitra™ and Cialis™.

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

Involvement of the PKG Pathway in Ion Channel Regulation

Nitric oxide (NO) is produced by various NO synthases (NOS), some of which are activated by a rise in intracellular $Ca^{2+}$. Many NO effects are mediated through direct activation of the soluble guanylyl cyclase (sGC), an enzyme generating the second messenger cyclic guanosine-3',5'-mono-phosphate (cGMP). sGC is stimulated by NO to catalyze the formation of cGMP. cGMP is a cyclic nucleotide second messenger with effects on many pathways, one of which is the PKG pathway. PKG is an enzyme that transfers a phosphate group from ATP to an intracellular protein, increasing or decreasing its activity.

Both the DNA sequence and protein function of PKG are conserved across the animal kingdom including mammals. PKG genes have been isolated from various animals spanning a wide variety of taxa ranging from humans (Sandberg et al., FEBS Lett 251:191-196, 1989) to even the malaria-causing protozoans *Plasmodium falciparum* (Gurnett et al., J Biol. Chem. 277:15913-15922, 2002). The protein phylogenetic analysis using 32 PKG sequences that include 19 species has shown the highly conserved link between PKG and behaviour in fruit flies, honey bees and nematodes (Fitzpatrick et al., Integr. Comp. Biol. 44:28-36, 2004).

Compositions for Treating Neural Anoxia and Spreading Depression

Compositions for protecting neural tissue from anoxia and SD are described herein. In a typical embodiment, a composition for protecting neural tissue from anoxia and SD includes a pharmacological inhibitor of the PKG pathway for treating one or both of neural anoxia and spreading depression. A composition can further include a pharmacologically acceptable excipient. Any suitable pharmacological inhibitor of the PKG pathway can be used. In some embodiments, the pharmacological inhibitor is a cGMP-specific antagonist, e.g. an antagonist that stimulates the activity of a phosphodiesterase, for example, PDE5 or PDE9, in the breakdown of cGMP. The pharmacological inhibitor may be an inhibitor of $K^+$ ion channel function. The pharmacological inhibitor may be a protein phosphatase inhibitor.

A number of pharmacological inhibitors of the PKG pathway are known; these inhibitors effect different points in the enzyme pathway. A pharmacological inhibitor of the PKG pathway suitable for the present invention may be a PKG inhibitor, for example: KT5823 ((9S, 10R, 12R)-2,3,9,10,11, 12-Hexahydro-10-methoxy-2-9-dimethyl-1-oxo-9,12-epoxy-1H-diindolo-[1,2,3-fg:3',2',1'-k1]pyrrolo[3,4-i][1,6] benzodiazocine-10-carboxylic acid methyl ester) (available from Sigma-Aldrich); H-9 dihydrochloride (N-(2-Aminoethyl)-5-isoquinolinesulfonamide hydrochloride) (available from Sigma-Aldrich); (Rp)-8-bromo-PET-cyclic GMPS (Guanosine 3',5'-cyclic Monophosphorothioate, β-Phenyl-1, $N^2$-etheno-8-bromo-, Rp-Isomer); (Rp)-8-pCPT-cylic GMP-S,TEA (Guanosine 3',5'-cyclic Monophosphorothioate,8-(4-Chlorophenylthio)-, Rp-Isomer, Triethylammonium Salt); Rp-8-Br-cGMPS, Na (Guanosine 3',5'-cyclic Monophosphorothioate, 8-Bromo-, Rp-Isomer, Sodium Salt); DT-3 [Antennapedia Homeodomain fused peptide (protein kinase G 1α inhibitor with the amino acid formula RQIKIWFQNRRMK-WKK-LRKKKKKH) (SEQ ID NO:1)]; DT-2 [HIV1-tat-W45 fused peptide with the amino acid formula YGRKKRRQRRRPP-LRKKKKKH (SEQ ID NO:2) (the protein inhibitor consisting of the Human Immunodeficiency Virus 1 Membrane Translocation Sequence (47-59) (YGRKKRRQRRRPP) (SEQ ID NO:3) fused with protein inhibitor W45 (LRKKKKKH) (SEQ ID NO:4)]; and the protein inhibitor having the amino acid formula RKRARKE (SEQ ID NO: 5) (sequence corresponds to a non-phosphorylatable analog ($Ser^{32}$ to $Ala^{32}$) of histone H2B (residues 29-35)). Suitable protein phosphatase inhibitors include, for example, Okadaic acid, Microcystin, Calyculin, and Cantharidin (Hexahydro-3a,7a-dimethyl-4,7-epoxyisobenzofuran-1,3-dione). The pharmacological inhibitor may be a sGC inhibitor, for example, 4H-8-Bromo-1,2,4-oxadiazolo (3,4-d) benz(b)(1,4)oxazin-1-one (NS 2028), 1H-[1,2,4] Oxadiazolo[4,3-a]quinoxalin-1-one (ODQ) or 6-Anilino-5, 8-quinolinequinone (LY83583).

These PKG pathway inhibitors are commercially available; a leading supplier is Calbiochem (EMD) Biosciences, San Diego, Calif. It will be recognized by those of skill in the art that certain of the aforementioned inhibitors are known in certain forms to have toxic effects, which must be addressed through formulation of the composition, as is known to those of skill in the art.

The compositions described herein are suitable for treating a number of medical conditions including damage from environmental hypoxia, spinal cord injury, stroke and migraine. Within minutes of a spinal cord injury, for example, a series of cellular processes contribute to further injury causing secondary damage. The mechanisms for this include inflammation resulting in restricted oxygenated blood flow resulting in nervous system anoxia at the site of injury and, accordingly, a patient suffering from a spinal cord injury can benefit from treatment with a composition or method as described herein.

As another example, the compositions described herein can be used to mitigate or prevent one or more side effects associated with a pharmaceutical composition that modules a nitric oxide/cyclic guanosine monophosphate pathway. Pharmaceutical compositions that module a nitric oxide/cyclic guanosine monophosphate pathway include drugs that are used to treat erectile dysfunction and angina. Side effects from use of a pharmaceutical composition that modules a nitric oxide/cyclic guanosine monophosphate pathway include dizziness, headache, and migraine. In some embodiments, a pharmaceutical composition as described herein includes a composition for treating erectile dysfunction or angina, and a pharmacological inhibitor of the PKG pathway in an amount effective for treating or preventing one or both of neural anoxia and SD. The pharmaceutical composition can further include a pharmacologically acceptable excipient. Examples of compositions for treating erectile dysfunction or angina include, e.g., phosphodiesterase type 5 inhibitors, nitrates, vasodilators, and nitroglycerine. Commercially available phosphodiesterase type 5 inhibitors include sildenafil, tadalafil and vardenafil.

Methods of Protecting Neural Tissue in a Patient

Described herein are methods of protecting neural tissue in a patient. The compositions and methods described herein can be used to provide immediate and significant protection to neurons enduring anoxic stress and spreading depression events. These methods can be used to protect neural tissue in a patient having a condition characterized by hypoxic insult to a neurological tissue. Stroke, for example, is a human pathology that results in oxygen deprivation to brain cells. During the acute phase shortly after the onset of an ischemic stroke, tissue in the penumbra surrounding an infarct receives sufficient blood flow to survive, but not enough to function. As time passes, neurons in this penumbra die. The time between anoxic neuronal failure and cell death provides a window of opportunity for the protection of neural function until return to normal oxygen levels. Providing neural anoxia protection can include lowering the level of oxygen at which neural function becomes abnormal, increasing the time before neural function becomes abnormal when subjected to anoxia, and reducing the precursor symptoms of neural failure. As shown in the Examples below, it was discovered that inhibition of the PKG pathway mediates protection in nervous systems under anoxic stress.

As another example of a condition that can be treated using compositions and methods described herein, increasing evidence from investigations in human subjects suggests that typical migraine auras may be the clinical manifestation of a cortical spreading depression (CSD)-like phenomenon. In mammalian tissue, CSD has been associated with several important pathologies including stroke, seizures and migraine. Providing protection from spreading depression protection can include increasing the time before neural function becomes abnormal when subject to increased extracellular $K^+$ or reduced $Na^+/K^+$ exchange. In a typical embodiment of treating a patient experiencing a migraine or susceptible to experiencing a migraine, a pharmacological inhibitor of the PKG pathway is administered to the patient susceptible to or having experienced anoxic stress, the PKG pathway inhibitor regulating potassium channel conductances and mitigating the extent and symptoms of the migraine. In the Examples below, the discovery that inhibition of the PKG pathway mitigates the onset of CSD-like (i.e. spreading depression) events is shown.

Methods of Mitigating the Side Effects of Pharmaceutical Compositions that Modulate the Nitric Oxide/Cyclic Guanosine Monophosphate Pathway In the Examples below, it was demonstrated that inhibition of the PKG pathway can mitigate side effects associated with some pharmaceutical treatments, specifically, pharmaceuticals that activate the NO/cGMP pathway. Methods of mitigating the side effects of pharmaceutical compositions that modulate the nitric oxide/cyclic guanosine monophosphate pathway include administering a therapeutically effective amount of a PKG pathway pharmacological inhibitor to a patient being treated for erectile dysfunction or angina, or to a patient that has been or will be treated for erectile dysfunction or angina. For example, the inhibitor can be a selective inhibitor of a cGMP specific phophodiesterase and, in some embodiments, is a selective inhibitor of PDE5. Administering a selective inhibitor of a cGMP specific phophodiesterase (e.g., a selective inhibitor of PDE5) can be used to treat erectile dysfunction. Examples of selective inhibitors of PDE5 include sildenafil, tadalafil and vardenafil.

Such drugs as sildenafil (Viagra™) and nitroglycerine are used for treatment of penile dysfunction or angina. Part of the physiological process of erection involves the parasympathetic nervous system causing the release of NO in the corpus cavernosum of the penis. NO binds to the receptors of GC which results in increased levels of cGMP and smooth muscle relaxation in the corpus cavernosum resulting in increased inflow of blood and an erection. Sildenafil (Viagra™), tadalafil (Cialis™) and vardenafil (Levitra™) are selective inhibitors of cGMP specific phosphodiesterase type 5 (PDE5) which is responsible for biodegradation of cGMP in the corpus cavernosum. These products act as competitive binding agents to cGMP of PDE5 in the corpus cavernosum. The compounds are selective for PDE5 over other phophodiesterase isoforms. In addition to being found in cavernosum smooth muscle, the PDE5 enzyme is found in vascular and visceral smooth muscle, skeletal muscle, platelets, kidney, lung, and cerebellum. These pharmaceutical products for treating erectile dysfunction can be associated with certain side effects.

The compositions and methods described herein can mitigate side effects by decreasing the cGMP response. In one embodiment, a composition for mitigating the side effects of pharmaceutical compositions that modulate the nitric oxide/cyclic guanosine monophosphate pathway can include at least one vasodilator.

Examples of side effects that can be mitigated by the compositions and methods described herein include headache, dizziness and abnormal vision. A composition including an inhibitor of the PKG pathway can be administered before, concurrently or after the administration of a pharmaceutical including an inhibitor of the cGMP specific phosphodiesterase. The method of administering a PKG pathway inhibitor is not particularly restricted and, without being limited thereto, the PKG pathway inhibitor could be administered orally, intravenously or via a transdermal patch.

Typically, a composition for mitigating the symptoms of at least one side effect associated with the administration of a pharmaceutical for the treatment of erectile dysfunction as described herein includes a PKG pathway inhibitor and a pharmaceutical excipient. In another embodiment, a composition as described herein includes a pharmaceutical agent for the treatment of erectile dysfunction, a PKG pathway inhibitor, and a pharmaceutical excipient. A pharmaceutical agent for the treatment of erectile dysfunction can be any suitable pharmaceutical agent, including a PDE5 inhibitor, e.g., sildenafil, tadalafil and vardenafil.

Another condition associated with the NO/cGMP pathway is Angina pectoris ("angina"). Angina is chest pain due to ischemia of the heart muscle, generally due to obstruction or spasm of the coronary arteries. Vasodilators are one category of pharmaceuticals that may be used in the treatment of angina. Vasodilators relax the smooth muscle in blood vessels, which causes them to dilate: dilation of arterial blood vessels leads to a decrease in blood pressure. Such vasodilators include nitrovasodilators, nitrates which undergo denitration to liberate nitric oxide. A commonly used vasodilator for the treatment of angina is nitroglycerine. Other vasodilators whose side effects can be mitigated by the methods and compositions of the present invention include, without being limited thereto, pentaerythritol tetranitrate (PETN); sodium nitroprusside (SNP); isosorbide mononitrate (ISMN); and isosorbide dinitrate (ISDN). Nitrates are used both to treat acute symptoms of angina and for the long-term prophylactic management of stable angina. A common side effect of nitrates is headaches due to dilation of cerebral vessels.

In one embodiment, a pharmaceutical agent for the treatment of angina is a nitrate which undergoes denitration to liberate nitric oxide. Examples of pharmaceutical agents for treating angina include nitroglycerine, PETN, SNP, ISMN and ISDN. Typically, a method for mitigating at least one side effect associated with the administration of a pharmaceutical agent for the treatment of angina that manipulates the NO/cGMP pathway includes the administration of an inhibitor of the PKG pathway. In some embodiments, a composition including a PKG pathway inhibitor and a pharmaceutical excipient is administered. In another embodiment, a pharmaceutical composition as described herein includes a pharmaceutical agent for the treatment of angina, a PKG pathway inhibitor, and a pharmaceutical excipient. For example, a pharmaceutical agent for the treatment of angina can include a pharmaceutical composition including nitroglycerine, a PKG pathway inhibitor and a pharmaceutical excipient. In the methods described herein, the inhibitor of the PKG pathway may be administered before, concurrently or after the administration of the pharmaceutical agent administered for the treatment of angina. Methods of administering the PKG pathway inhibitor are not particularly restricted and, without being limited thereto, the PKG pathway inhibitor could be administered orally, intravenously or via a transdermal patch.

Administration of Compositions

The manner of administering a composition as described herein to a patient is not specifically restricted, and various methods will be readily apparent to persons skilled in the art. The composition, for example, could be delivered by injection, intravenously, intramuscularly, intraperitoneally, topically, subcutaneously, rectally, dermally, sublingually, buccally, intranasally or via inhalation to a patient. Oral administration would be particularly suitable where compositions of the present invention are taken as a prophylactic. Solid dosage forms for oral administration of the compositions of the present invention include, but are not limited to, ingestible capsules, tablets, pills, lollipops, powders, granules, elixirs, suspensions, syrups, wafers, sublingual or buccal tablets, troches, and the like. In such solid dosage forms, the PKG pathway inhibitor is mixed with at least one inert, pharmaceutically acceptable excipient, diluent or edible carrier. In the case of intravenous formulations expected to be useful in the present invention, these include, but are not limited to, sterile aqueous solutions (where water soluble) or dispersions and sterile powders for the extemporaneous preparation of sterile injectable solutions or dispersions. In all cases, the compositions must be stable under the conditions of manufacture and storage and should be preserved against the contaminating action of microorganisms such as bacteria and fungi.

The pharmaceutical composition of the present invention can include any suitable excipient, as will be ascertainable by a person skilled in the art. In certain embodiments of the present invention, the composition includes inhibitors modified to improve solubility and cell permeability through packaging with modifying agents such as Membrane Translocation Proteins, esterification such that the esterified compound passes through lipid membranes and is converted into the active form in the cell by constitutive esterases, and the use of alternative salts of acid or basic compounds to improve solubility, stability, or buffer pH, changes which are apparent to persons skilled in the art upon reference to this description as means of improving stability, solubility, and delivery to the cell of the pharmacological inhibitors.

A non-limiting example of an effective dose range for a pharmaceutical composition as described herein is 0.01-500 mg/kg of body weight per day, more preferably 0.01-50 mg/kg of body weight per day, and still more preferably 0.05-50 mg/kg of body weight per day. In an aqueous composition, preferred concentrations for the active compound are 10 µM-500 mM, more preferably 10 µM-100 mM, still more preferably 10 µM-50 mM, and still more preferably 100 µM-50 mM.

EXAMPLES

Example 1

*Locusta migratoria* Experiments

CSD is increasingly accepted as a primary causative agent for migraine, particularly migraine with aura. The cellular mechanisms underlying stroke, seizures and migraine are not exclusive to mammals. Using the locust (*Locusta migratoria*), a proven model for examining the effects of heat stress on CNS activity, a rapid rise in extracellular potassium ([K$^+$]$_o$) during anoxia/hypoxia, extreme heat, and ouabain exposure was monitored. This phenomenon has all the characteristics of SD in the neocortex of mammals. Since the physiological mechanisms observed in locust SD-like events are similar to that of mammals, findings in this insect model are predictably transferable to mammals, including humans. In the locust, model SD-like events were triggered in the CNS by injecting small volumes of saline containing high levels of potassium ions (KCl at 150 mM instead of the nominal resting level of 10 mM) into the metathoracic ganglion. Potassium-sensitive microelectrodes were used to measure SD generated by KCl injections, while manipulating the PKG pathway. Following a bath application of KT5823 (PKG antagonist) ($10^{-5}$M), which is a potent inhibitor of PKG-mediated effects, a significant reduction in the length of time in SD was observed, whereas animals treated with T-0156 (phosphodiesterase inhibitor (PDE5/6)) ($10^{-5}$M), which potentiates the PKG pathway by preventing the breakdown of cGMP, stayed in SD for a significantly longer time than control animals.

As shown in FIG. 1A, injection (see Trigger line) of 50 nL of saline containing elevated potassium (KCl at 150 mM) evoked SD-like events in the metathoracic ganglion of the locust. This tissue response is characterised by a transient surge and subsequent clearance of potassium ions in the extracellular space ([K$^+$]$_o$). During SD-like events ventilatory motor activity ceases. This was monitored using an electromyographic electrode positioned on an abdominal muscle used for ventilation (Ventilatory EMG). Upon restoration of the potassium ion gradient the neural activity recovered and preparations began to ventilate again. Expansions of the traces demonstrate ventilatory motor activity at about 1 cycle/s.

As shown in FIG. 1B, to examine the effect on SD of different drug treatments, all preparations received two injections of high potassium into the metathoracic ganglion. The first injection was used as a control. Following the first injection, animals were allowed 10 minutes of perfusion with standard locust saline before treatment with bath applications of selected drugs (i.e. KT5823, T-0156). All drugs were dissolved in a minimum amount of DMSO before further dilution with standard locust saline to a concentration of $10^{-5}$M and were superfused over the metathoracic ganglion for 10 minutes before the second injection. A total of 20 minutes elapsed between the first and second injection in all experiments. As shown in Figure (Bi), duration at half the maximum amplitude was used to characterize the severity of SD-like events. A significant increase was observed following the second injection when compared to the first in control animals. The increase was dramatically greater in T-0156-treated (increases cGMP) preparations. Treatment with KT5823 (PKG antagonist) reduced SD duration after the second injection. Heat shock (HS) preconditioning reduced SD duration evoked by the first and second injections. Cantharidin (PP2A antagonist) blocked the effect of T-0156 (see T-0156/Can in Figures). Numbers in the histogram bars indicate number of preparations tested. Asterisks indicate statistically significant differences between the first and second injection (P>0.05). As shown in Figure (Bii), percentage difference in SD duration (second injection relative to first injection) shows more clearly the treatment effects.

As shown in FIG. 1C, a second measure used to characterize the severity of SD was the length of time taken to recover ventilatory motor pattern activity. Motor pattern activity was not measured for T-0156/Cantharidin treatments. When tested, it is expected that the application of Cantharidin will rescue the detrimental affects of T-0156. As shown in Figure (Ci), untreated preparations and those treated with T-0156 took significantly longer to recover motor pattern activity after the second injection than preparations that received HS-preconditioning and those treated with KT5823. Figure (Cii) illustrates the drug effects by showing the percentage difference in rhythm recovery time (second injection relative to first injection).

Example 2

KT5823 Treatment Prevents Repetitive SD in Ouabain-Treated Animals

In a second set of experiments, repetitive SD triggered by the ionic disturbance caused by ouabain (a specific inhibitor of the sodium/potassium pump that restores ionic gradients across cell membranes) was examined. As shown in FIG. 2A, repetitive SD was generated in 100% of control animals and 8-Br-cGMP-treated (PKG activator) animals concomitantly treated with $10^{-4}$M ouabain and was monitored by recording ventilatory motor activity (Ventilatory EMG) and by recording extracellular potassium concentration in the metathoracic ganglion ([K$^+$]$_o$).

Pretreatment with a bath application of KT5823 prevented repetitive SD in 70% of animals. Of the animals that generated SD-like events, control (not treated with KT5823) animals had significantly more SD-like events than KT5823-treated animals, while control and KT5823-treated animals had significantly fewer SD-like events than 8-Br-cGMP-treated animals. FIG. 2B illustrates a representative example in a single preparation of the eradication of repetitive SD by prior bath application of KT5823. FIG. 2C illustrates that KT5823 reduced the percentage of preparations showing repetitive SD in response to ouabain, while FIG. 2D illustrates that control and KT5823-treated preparations have fewer repetitive SD events.

As shown in FIG. 2E, pre-treatment with the PKG inhibitor KT5823 significantly reduces the baseline [K$^+$]$_o$ levels during ouabain exposure compared with control and 8-Br-cGMP-treated animals. Activation of the PKG pathway with 8-Br-cGMP did not raise the baseline [K$^+$]$_o$ levels above controls.

These data confirm that the PKG pathway plays a crucial role in regulating SD in the CNS of locusts. The results demonstrate that inhibition of the PKG pathway greatly reduces SD in the locust model, while activation of the pathway with 8-Br-cGMP exacerbates SD pathology. Similar effects in humans would mitigate the underlying causes of migraine and headache as a side-effect of treatments for angina and erectile dysfunction. Further, by coupling the inhibition of the PKG pathway through the use of PKG or PP2A inhibitors directed specifically at the nervous system during use of a PDE5 inhibitor, the potential side effect of migraines could be mitigated before onset.

Example 3

Characterization and Mitigation of SD

Figure 3A:
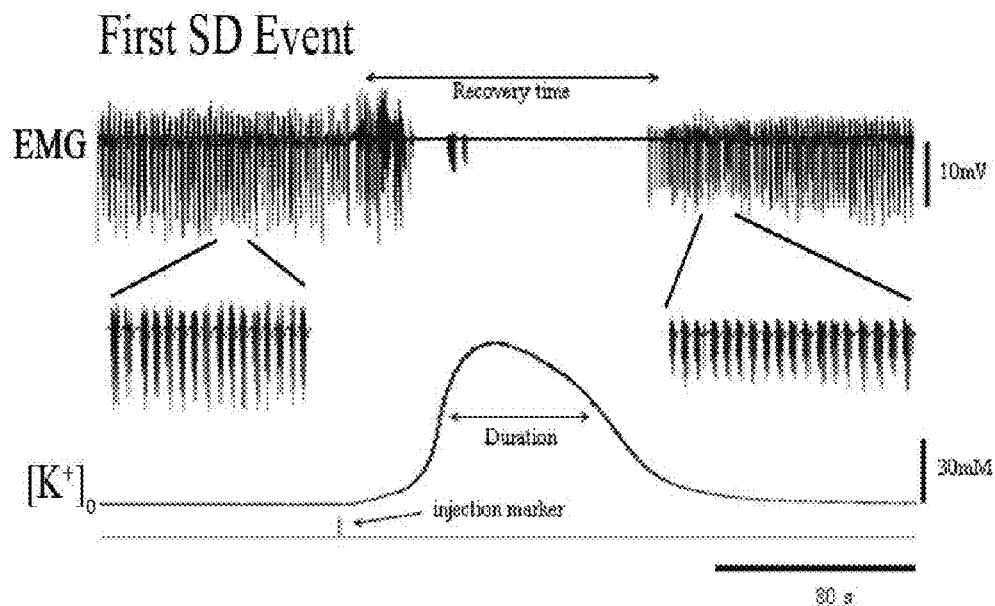
FIG. 3A is a plot illustrating Ventilatory EMG and extracellular potassium concentration in the metathoracic ganglion of the locust in which a first SD event was elicited by injection of saline containing elevated potassium chloride directly into the metathoracic ganglion.
Figure 3B:
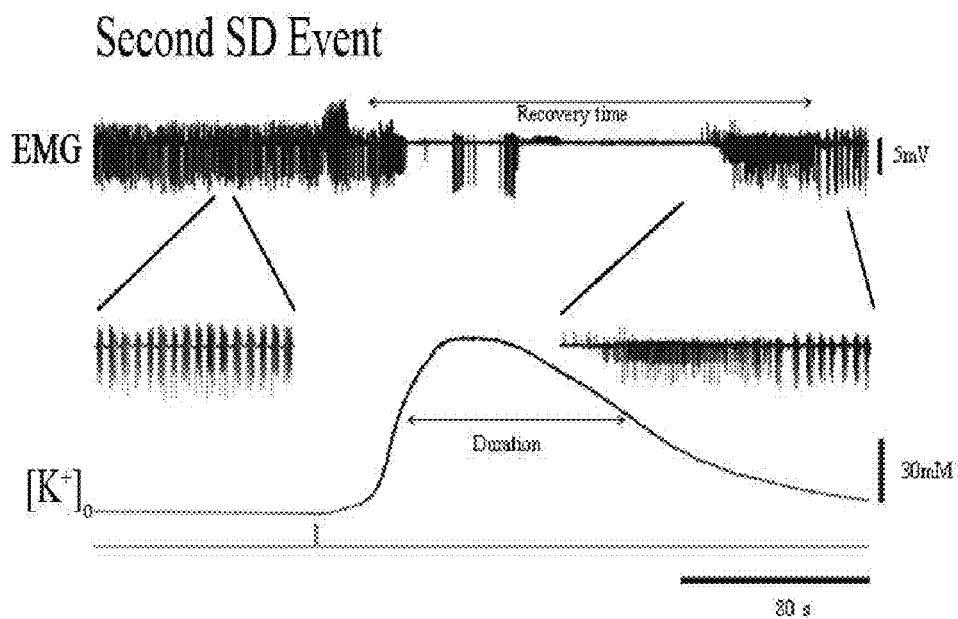
FIG. 3B is a plot illustrating Ventilatory EMG and extracellular potassium concentration in the metathoracic ganglion of the locust in which a second SD event was elicited 20 minutes following recovery of motor pattern from a first SD event. SD event was elicited by injection of saline containing elevated potassium chloride directly into the metathoracic ganglion.
Figures 3C, 3D:
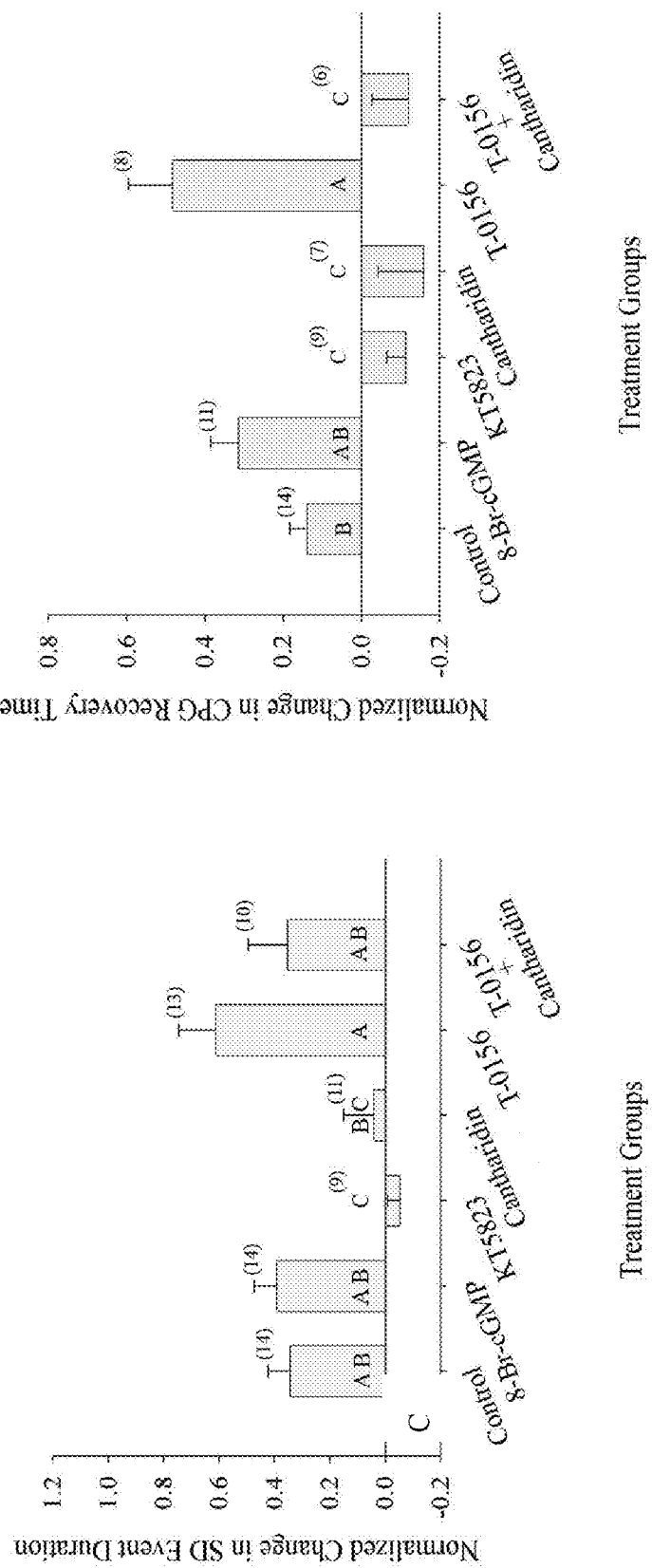
FIG. 3C is a graph illustrating the change in SD event duration as between a first SD event (FIG. 3A) and a second SD event (FIG. 3B) for control, 8-Br-cGMP-treated, KT5823, Cantharidin (protein phosphatase inhibitor), T-0156 (phosphodiesterase inhibitor) and T-0156+Cantharidin-treated animals. Error bars are ±SEM. Numbers in brackets represent sample sizes.
FIG. 3D is a graph illustrating the change in recovery time as between a first SD event (FIG. 3A) and a second SD event (FIG. 3B) for control, 8-Br-cGMP-treated, KT5823, Cantharidin, T-0156 and T-0156+Cantharidin-treated animals. Error bars are ±SEM. Numbers in brackets represent sample sizes.

Single SD events were evoked by injection of saline (50 nL) containing elevated potassium chloride (150 mM vs. 10 mM) directly into the metathoracic ganglion. As shown in FIG. 3A, SD was characterized by a wave-like transient increase of extracellular potassium ion concentration ([K$^+$]$_o$). During SD, ventilatory motor activity monitored electromyographically (EMG) ceased and recovered upon restoration of the potassium ion gradient. The duration of the [K$^+$]$_o$ wave at half its maximal amplitude and the time from failure of motor patterning to the recovery of a ventilatory rhythm were measured. As shown in FIG. 3B, 20 minutes following recovery of the motor pattern a second injection was delivered into the metathoracic ganglion evoking a second SD event and permitting within animal comparisons following various drug treatments applied for 10 minutes prior to the second injection. As shown in FIG. 3C, in control preparations, the second event was about 30% longer than the first. Event duration was increased by T-0156 (a phosphodiesterase inhibitor), though not by 8-Br-cGMP, and was reduced by KT5823 and cantharidin. The effect of T-0156 was offset by cantharidin. As shown in FIG. 3D, in control preparations, recovery time was about 10% longer for the second event compared with the first. The recovery time was increased by 8-Br-cGMP and T-0156 and was reduced by KT5823 and cantharidin. The effect of T-0156 was offset by cantharidin. These data indicate that PKG inhibition (KT5823) reduced the duration of SD and hastened the time to recover neural function following SD whereas activation of the pathway (8-Br-cGMP, T-0156) had the opposite effect. Numbers in brackets represent sample size. Letters in histogram bars represent statistical groupings using a post-hoc test, whereby bars with different letters are significantly different (Tukey, $p<0.05$).

Example 4

Inhibition of Nitric Oxide (NO) Production Reduces SD Pathology

In the experiments described herein, it was demonstrated that the production of NO by the locust CNS during stress and that inhibition of NO production reduces SD pathology in the locust CNS. As shown in FIG. 4A, the metathoracic ganglion of locusts were stained with diaminofluorescein-2-diacetate (DAF2-DA) to reveal NO-producing cells. The pattern of cell staining was similar to that of NOS staining in *Schistocerca gregaria* and *L. migratoria* (Müller and Bicker, The Journal of Neuroscience 14:7521-7528, 1994; Bullerjahn and Pflüger, Zoology 106:3-17, 2003). The scale in the Figure is 500 µm. FIGS. 4B and 4C show fluorescing cell bodies at room temperature (20° C.) (4B) and immediately following exposure to heat (35° C.) (4C) (scale for both Figures is 50 µm). The change in fluorescence following exposure to heat was quantified as shown in FIG. 4D (3 minutes at 35° C., shown by bar above x-axis). The difference between cell body fluorescence and background more than doubled immediately following exposure to heat (t=5 minutes). Treatment with the NO synthase inhibitor N(G)-nitro-L-arginine methyl ester (LNAME) (100 µM) prevented the increased fluorescence in response to heat stress. Fluorescence was measured from the brightest 3 cells from each ganglion. [Sample sizes: Control, n=7; LNAME, n=4; and No heat, n=3. Asterisks indicate significant differences of control from LNAME and No heat groups (Tukey, $p<0.05$).] As shown in FIG. 4E, chemical anoxia (treatment of cells with sodium azide, 1 mM) increased cell body fluorescence (sample sizes are indicated in brackets).

Example 5

Figure 5:
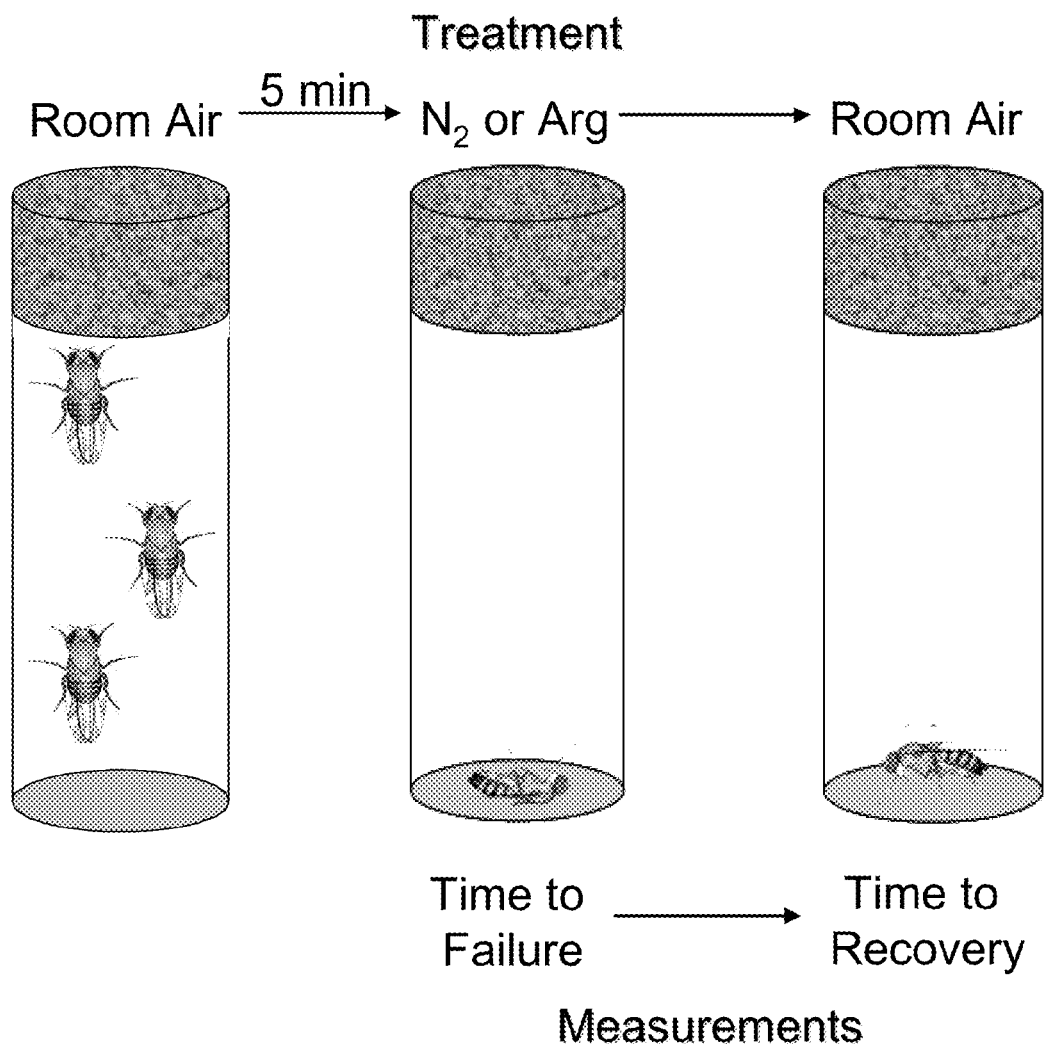
FIG. 5 illustrates the anoxia protocol used on *Drosophila melanogaster*.

Confirmation that Inhibition of the NO Pathway Regulates SD in the CNS of Locusts As in Example 3, SD events were evoked by injection of saline (50 nL) containing elevated potassium chloride (150 mM vs. 10 mM) directly into the metathoracic ganglion of locust preparations. As shown in FIG. 5A, LNAME significantly reduced SD duration compared with control preparations. Preparations treated with the NO donor molecules (S-nitroso-N-acetyl-D-penicillamine (SNAP) and S-nitroso-glutathione (SNOG)) showed no significant change in SD duration when compared to control preparations. However, animals treated with SNOG showed significantly longer SD duration than the LNAME treated animals. Reduced recovery times generated as a result of LNAME treatment could be offset by co-treatment with SNOG (LNAME/SNOG). As shown in FIG. 4B, LNAME dramatically reduced the length of time taken to recover ventilatory central pattern generator (vCPG) function following SD. Treatment with SNAP or SNOG did not exacerbate recovery times beyond that of control preparation times. However, the reduced recovery time period observed following LNAME treatment was abolished in preparations co-treated with LNAME and SNOG (LNAME/SNOG).

The data of Examples 4 and 5 confirm that inhibition of the NO pathway, which is upstream of the PKG pathway, also regulates SD in the CNS of locusts. The results demonstrate that reduced production of NO also reduces SD severity, while activation of the pathway with 8-Br-cGMP exacerbates SD pathology.

Example 6

Modulation of Anoxic Coma Onset by a Single Major Gene

Over the past decade, global temperature changes have led to detrimental alterations in animal habitats. For example, there have been significant increases in the rate of growth of low-oxygen zones in the world's oceans. It is therefore crucial to find ways to mitigate the harmful physiological effects of low-oxygen exposure on animals, as well as understand the potential impact such environments may have on ecosystem sustainability. In the experiments described herein, it has been demonstrated that variation in the gene foraging (for), encoding a PKG, markedly alters low-oxygen tolerance during locomotion in adult *Drosophila melanogaster*. Reduced PKG activity, due to natural variation or induced mutation in the for gene, increases tolerance to acute hypoxia. Further, in vivo pharmacological manipulations using a novel volatilization technique revealed that reducing either PKG or protein phosphatase 2A (PP2A) activity increases tolerance of locomotory behaviour to acute hypoxic conditions. Alternatively, PKG activation, Phosphodiesterase (PDE) 5/6 inhibition, and Dicholoroacetate (DCA) treatment, enhance sensitivity to acute hypoxia. Importantly, the novel pathway described shows the means for detecting and manipulating acute low-oxygen tolerance.

The hypothesis that natural variation in expression and activity levels of PKG, encoded by the foraging gene, modulates acute low-oxygen tolerance during locomotory behaviour in adult *Drosophila melanogaster* was examined. Using both genetics and pharmacology, the roles and order of function of additional cGMP-dependent signaling molecules in determining acute low-oxygen sensitivity of locomotory failure were examined. To do this, acute hypoxia was imposed on the animals by displacing environmental oxygen with the inert gas argon in a closed arena, and then time to failure of locomotion (anoxic coma) was measured, which can be observed in less than 2% atmospheric oxygen. In the past, this method has been overlooked due to rapid locomotory cessation (~30 secs) (Haddad G. G., J Appl Physiol. 88:1481-1487, 2000) in the absence of oxygen, but by slowing the rate of infusion of gas into an arena, this period has been extended by over ten-fold. A novel method of pharmacological volatilization was also used as a means to manipulate, in vivo, potential targets including PKG. The animals used in these assays were frozen immediately after each trial, and heads were examined for PKG activity, as an indicator for activity levels in the brain (Belay et al., J Comp Neurol. 504:570-582, 2007; Kaun et al., J Exp Biol. 210(Pt 20):3547-3558, 2007).

Figure 6A:
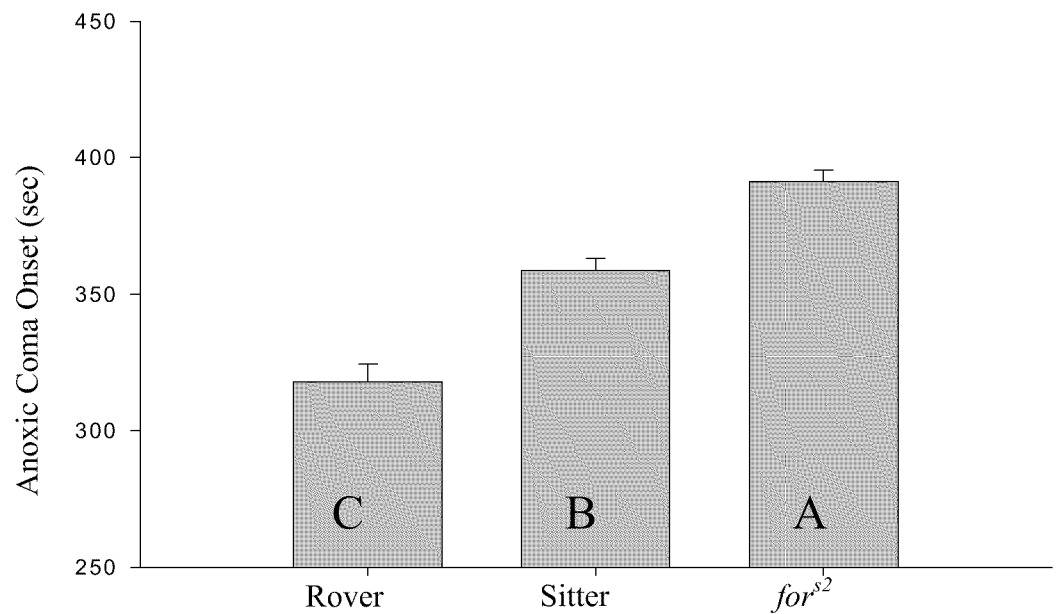
FIG. 6 is a series of graphs illustrating data that shows anoxic coma onset is modulated by PKG activity through natural variation of the foraging gene upstream of the effects of heat shock preconditioning. A) Time to anoxic coma onset (time to failure) in adult *Drosophila melanogaster* during acute hypoxia by air displacement using pure argon gas, was significantly increased in the natural allele of the foraging gene, sitter (N=18; low PKG activity), when compared with rover (N=18; high PKG activity). Further, for$^{s2}$ (N=18), a foraging mutant in rover (low PKG activity), was also significantly resilient to acute hypoxia when compared to the two natural alleles (One-Way ANOVA, $F_{(2,51)}=50.352$, $p<0.001$; Multiple Comparisons, SNK, $p<0.05$). B) PKG activity was assayed from the heads of animals in A), confirming that rovers exhibited high PKG activity, whereas sitters and for$^{s2}$ showed significantly lower PKG activity (N=6 for each genotype; One-Way ANOVA, $F_{(2,15)}=20.360$, $p<0.001$; SNK, $p<0.05$). C) After a heat shock preconditioning treatment using the three genotypes (see Online Methods), significantly increased resilience to anoxic coma onset was observed when compared with controls (N=24 for each genotype; Two-Way ANOVA, $F_{(2,120)}=14.375$, $p<0.001$; SNK, $p<0.05$). All vertical bar charts are shown as mean+/±s.e.m. Significant differences were established with $p<0.05$, where letters that differ on the graphs signify statistical groupings.
Figure 6B:
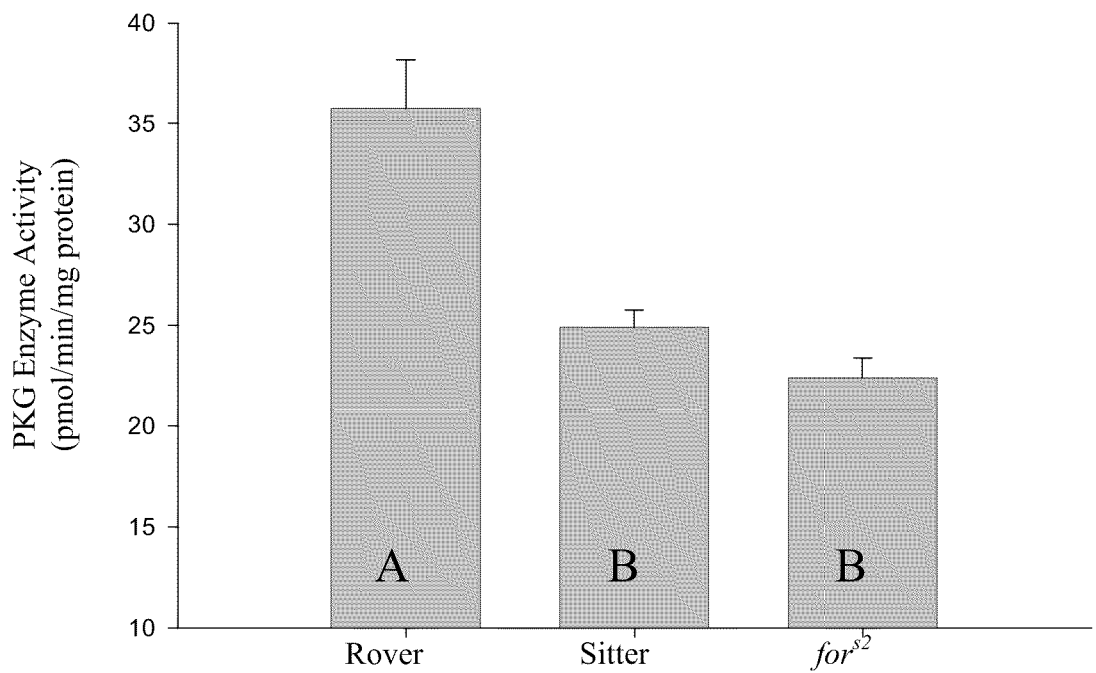

To examine a potential role for PKG in regulating sensitivity to acute hypoxia, flies representing two natural alleles of the foraging gene, rover (high PKG activity) and sitter (low PKG activity), were assayed along with for$^{s2}$, a hypomorphic foraging mutant on a rover background, for locomotion failure. Rover flies were found to fail significantly sooner than sitter and for$^{s2}$ under acute low-oxygen exposure (FIG. 6A), suggesting that foraging alleles exhibiting lower PKG activity are associated with increased resilience of locomotory behavior during acute hypoxia, similar to what is found during hyperthermic stress. PKG enzyme activity assays verified that PKG activity levels were increased in rover fly heads compared to other genotypes, (FIG. 6B).

Figure 6C:
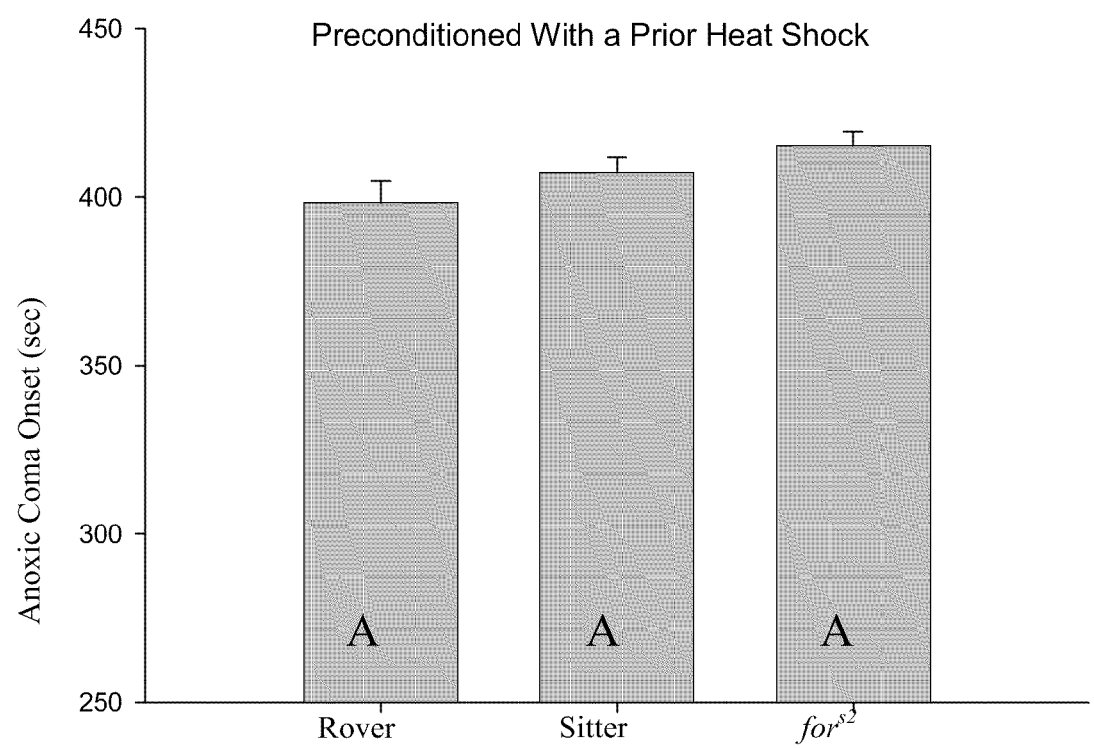

The heat shock or stress response in organisms ranging from protozoans to humans can be induced by the short exposure of a non-lethal increase in temperature sufficient for causing the up-regulation of heat shock proteins. This endogenous type of preconditioning has been implicated in the protection of organisms to a variety of stresses including cerebral ischemia, cold ischemia, and hyperthermia. Therefore, the limits of locomotory tolerance to acute hypoxia in the three genotypes were tested with a heat shock preconditioning treatment. Adult flies were preconditioned using a previously described heat shock protocol (Karunanithi et al., J Neurosci. 19:4360-4369, 1999) where maximal up-regulation of HSP70 in *Drosophila* larvae occurs following a 1 hour exposure to 36° C. with a 30 minute recovery. In the three genotypes tested, rovers, sitters, and for$^{s2}$, the preconditioned flies demonstrated significant resilience to locomotory failure during acute hypoxia with no difference across genotypes (FIG. 6C). The time for locomotion to fail was significantly greater in the preconditioned animals than untreated rovers, sitters, and for$^{s2}$ (FIG. 6A).

Figure 8A:
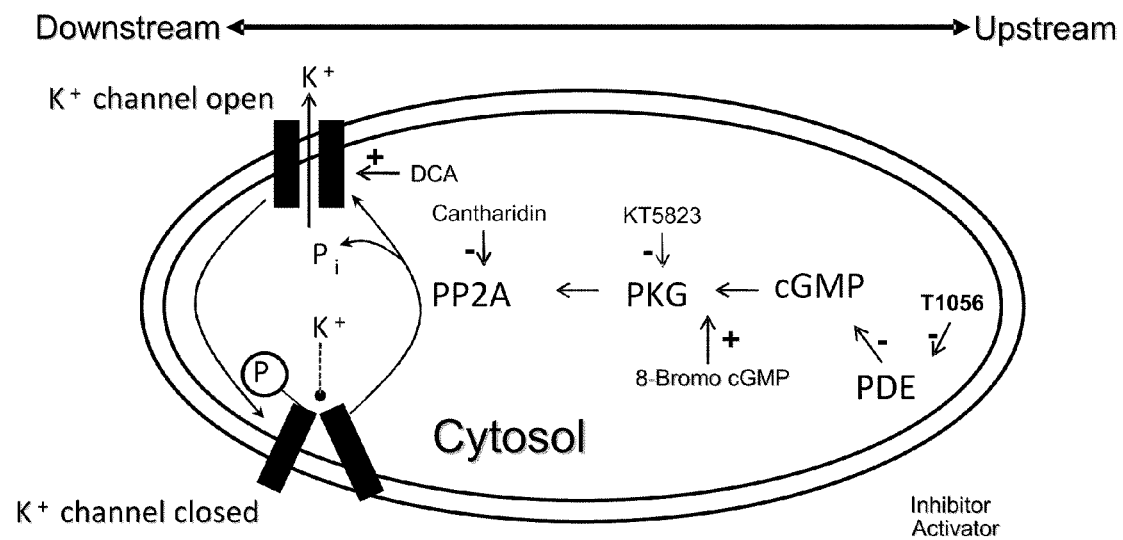
FIG. 8A is a diagram adapted from Zhou et al. (J. Biol. Chem. 271:19760-19767, 1996) that represents upstream and downstream intracellular targets for manipulating the PKG pathway partially implicated in the modulation of hyperthermic stress[8]. Protein phosphatase 2A (PP2A), PKG, cyclic GMP (cGMP), phosphodiesterases (PDE), and K$^+$ channels are shown as potential targets for pharmacological manipulation. Inhibitory compounds are shown with a minus (−) sign, while activators are shown with a plus (+) sign. The diagram shows that molecular targets and pharmacological compounds to the left are downstream of those on the right, as shown by the large double arrow at the top of the diagram.
Figure 9:
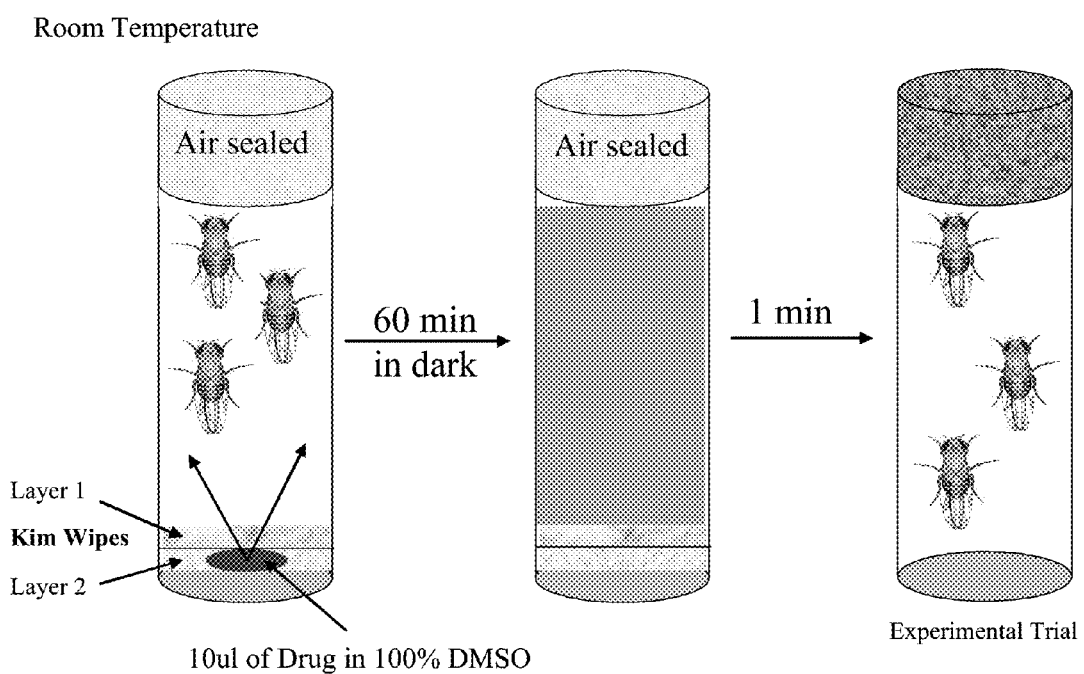
FIG. 9 is a diagram illustrating in vivo treatment of adult *Drosophila melanogaster* with pharmacological agents. 5-9 day old adult *Drosophila melanogaster* that were exposed to the pharmacological agents, volatilized from 10 uL of DMSO at room temperature for 60 minutes in the dark, had significant and predictable tolerances to anoxic coma onset (FIGS. 7A, 8B). Adult sitters were exposed to various drugs known to target components of the PKG pathway (FIG. 8A). These drugs included: 10 mM T0156, a cGMP-specific phosphodiesterase-5 inhibitor, 10 mM 8-Bromo-cGMP, a PKG activator, 1 mM KT5823, a PKG inhibitor, 1 mM Cantharidin, a PP2A inhibitor, and 200 mM DCA, a K$^+$ channel activator. All drugs were solubilized in dimethyl sulfoxide (DMSO), where flies treated with only DMSO were used as sham controls. Drugs were administered to whole adults in vivo through volatilization at concentrations 10-fold higher than those used in vitro (Dawson-Scully et al., PLoS ONE, 2(1): e773, 2007). 10 µL of drug solution was applied to a crushed Kim wipe at the bottom of each 10 mL test vial. An additional Kim wipe was crushed over top of this to prevent direct contact between the fly and solution. 10 flies were then placed in the vial which was capped with a semi-permeable buzz-stopper, covered with a cut-out finger of a large latex glove to prevent chemical vapours from escaping, and incubated in the dark. The flies were subjected to the drug for 1 hr prior to each behavioural assay. In the drug combination experiments, 20 uL of DMSO was used as a control sham, and combinations of two pharmacological treatments were added as two separate 10 uL aliquots.

Whether or not fly PKG levels could be manipulated in vivo using a technique that uses volatilization of pharmacological agents was next examined. The role of these targets in vivo using sitter flies was examined by depositing pharmacological agents dissolved in DMSO on a cellulose tissue, and allowing them to volatize over minutes in an air tight vial at room temperature (FIG. 9). Adults were exposed to the volatilized compound for one hour in the dark and then assayed for locomotory resilience to acute hypoxia. Control sham animals (FIG. 7A) were treated with only DMSO. Compounds were chosen to target different components of the cGMP pathway (FIG. 8A) in tracheal smooth muscle and Chinese hamster ovary cells, where cGMP activates PKG, thereby activating PP2A, which then de-phosphorylates K$^+$ channels. The hypothesis that inhibition of this pathway would result in an increase in whole cell K$^+$ channel conductance, thereby leading to increased resilience to anoxic coma onset, was tested.

Figure 7A:
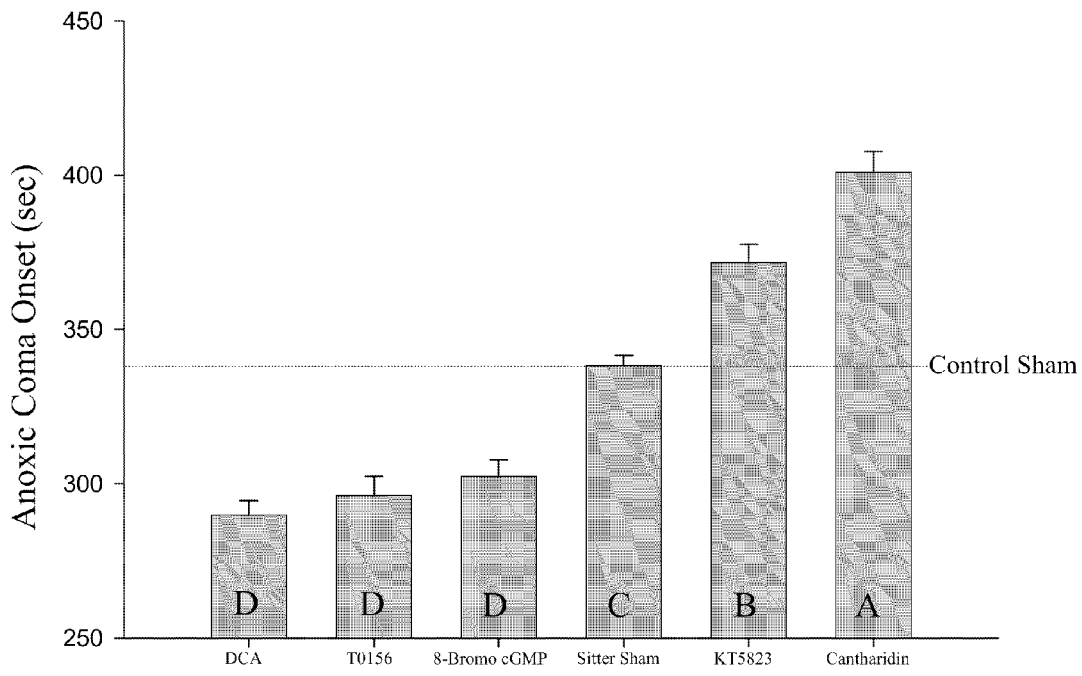
FIG. 7 is a pair of graphs illustrating data that shows in vivo pharmacological manipulation of various molecular targets in the PKG pathway modulates time to anoxic coma onset during acute hypoxia. A) Various volatilized pharmacological agents were used in vivo on the intermediate resilient allele sitter, to determine how different molecular targets modulate anoxic coma onset during acute hypoxia. Each treatment had a significant effect, either increasing or decreasing anoxic coma onset sensitivity (Kruskal-Wallis, $H_{(5)}=107.454$, $p<0.001$; Multiple Comparisons, Dunn's, $p<0.05$), where 1 mM KT5823/[−]PKG (N=47; pharmacological agent/[+ activates/− inhibits]target) and 1 mM Cantharidin/-PP2A (N=12) demonstrated significant resilience to anoxic coma (Dunn's, $p<0.05$) and 200 mM DCA/[+]K$^+$ channels (N=15), 10 mM 8-Bromo cGMP/[+]PKG (N=34), and 10 mM T-0156/[−]PDE5/6 (N=16) exhibited significant sensitivity to anoxic coma (Dunn's, $p<0.05$). B) PKG enzyme activity assays on heads of animals derived from experiments that showed that agents which could manipulate PKG either directly such as 8-Bromo cGMP/[+]PKG and KT5823/[−]PKG or indirectly such as T0156/[−]PDE5/6 (which would increase intracellular cGMP) demonstrated significant effects compared to that of the sham control (N=6 for each treatment; One-Way ANOVA, $F_{(5,30)}=20.898$, $p<0.001$; SNK, $p<0.05$). However, targets that were downstream of PKG (see FIG. 8A), such as Cantharidin/[−]PP2A and DCA/[+]K$^+$ channels, showed no significant effects on PKG enzyme activity levels compared to sham controls (SNK, $p>0.05$). All vertical bar charts are shown as mean+/−s.e.m. Significant differences were established with $p<0.05$, where letters that differ on the graphs signify statistical groupings. Horizontal dotted line represents mean of sham control for ease of comparison across treatments.
Figure 7B:
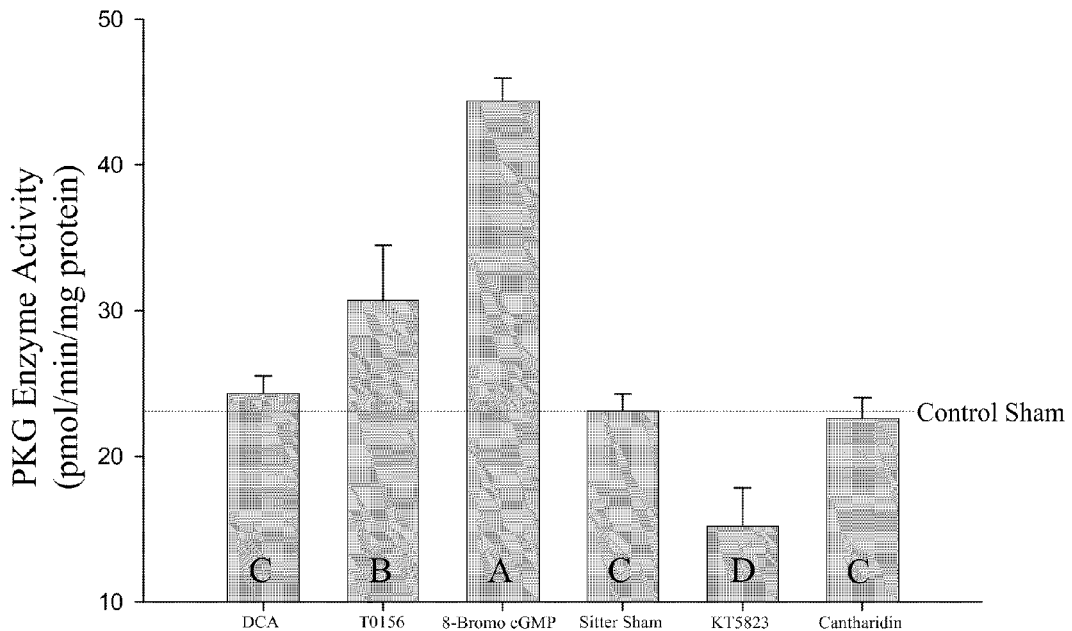

Initially, the PKG activator 8-bromo cGMP was used, which induced an increase in head PKG activity levels and, as expected, enhanced sensitivity to acute hypoxia (FIG. 7A, B). This treatment expedited locomotory failure during acute hypoxia of sitters to rover levels, while increasing head PKG activity levels significantly beyond rover levels. Animals treated with the PDE 5/6 inhibitor, T0156, similarly showed an increased sensitivity to acute hypoxia, as well as a significant increase in PKG activity levels compared with sitter control shams. In contrast, treatment with a PKG-specific inhibitor, KT5823, had the expected opposite effect, inducing a significant increase in tolerance to acute hypoxia and significantly reducing PKG activity. Similar locomotory tolerance was induced using a specific protein phosphatase 2A inhibitor (PP2A), Cantharidin. However, as expected, PKG activity levels did not differ in Cantharidin-treated animals compared with control shams. In order to examine the K$^+$ channel axis, a compound that has been shown to potentiate the nitric oxide (NO)/K$^+$ channel axis[18] in a number of cell types, Dichloroacetate[19,20] (DCA), was used. The hypothesis that increasing K$^+$ currents with dichloroacetate would cause an increase in sensitivity to acute hypoxia was tested. It was observed that the DCA treatment caused a decreased locomotory tolerance (FIG. 7A) to acute hypoxia, as well as no changes in head PKG enzyme activity levels as expected (FIG. 7B).

Figure 8B:
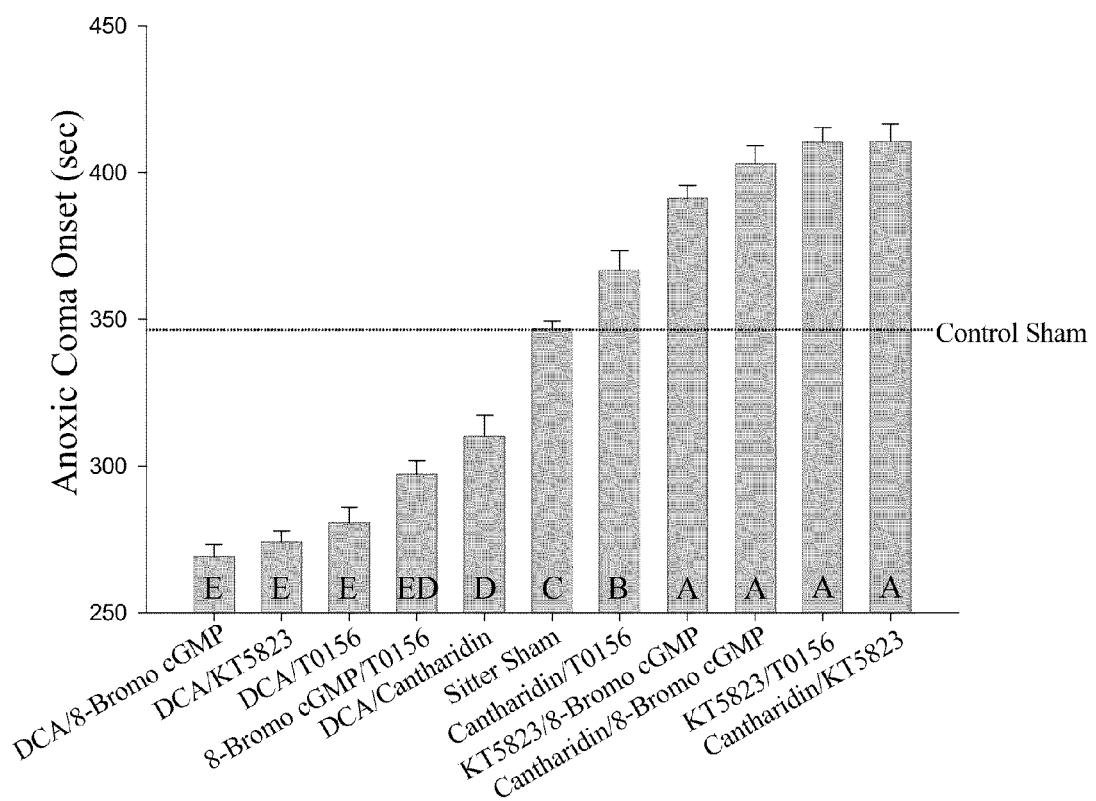
FIG. 8B is a graph illustrating data that shows that combinations of pharmacological agents that modulate time to anoxic coma onset during acute hypoxia reveal downstream and upstream molecular targets in the PKG pathway. Combinations of the pharmacological agents used, in vivo, shown in FIG. 7, were administered to adult *Drosophila melanogaster*, and then the animals were tested for resilience to anoxic coma onset during acute hypoxia. Similar to experiments using individual compounds (FIG. 7A), each combined treatment of two agents (see Table 1) either significantly increased or decreased anoxic coma onset sensitivity when compared to sham controls (One-Way ANOVA, $F_{(10,184)}=105.634$, $p<0.001$; SNK, $p<0.05$). As predicted, pharmacological agents that inhibited or activated downstream molecular targets, as shown in B), directed the anoxic coma onset phenotype. For example, anytime animals were treated with a combination of drugs that included DCA, a significant decrease in resilience to anoxic coma onset was observed, when compared to sham controls (SNK, $p<0.05$). Vertical bar chart is shown as mean+/−s.e.m. Significant differences were established with $p<0.05$, where letters that differ on the graphs signify statistical groupings. Horizontal dotted line represents mean of sham control for ease of comparison across treatments.

Next, two simultaneous pharmacological treatments of the above mentioned compounds in all complementary combinations were used to verify upstream and downstream components (FIG. 8A) of this proposed pathway (Table 1). The hypothesis that downstream molecular targets would have dominant phenotypes over upstream targets was tested. As an example, DCA treatment was expected to be dominant across all other targets, and the PDE 5/6 inhibitor T0156 was expected to have the weakest effect. With each drug combination, the compound that affected the proposed downstream target was indeed dominant, where each effect was significant (FIG. 8B). Interestingly, the combination of DCA and Cantharidin demonstrated intermediate protection of locomotory failure when compared with the combination of DCA and KT5823. It is possible that PP2A may in fact be one of many targets that affect K$^+$ channels modulated by DCA, through the effects of PKG activity levels.

Behavioural data presented herein suggests that a reduction in PKG or PP2A activity promotes increased tolerance to acute low-oxygen environments before anoxic coma occurs. Further, the data suggest that this pathway also acts through PDEs and DCA-sensitive K$^+$ channels. The natural polymorphism in the foraging gene appears to be important for the determination of limits for low-oxygen stress during behaviour of the fruit fly. Therefore, oxygen tolerance may have played a pivotal role in how the rover and sitter alleles have been maintained during evolution. Further, since the alleles differ in their ability to tolerate low-oxygen stress, ecological implications of habitat limitations and sudden environmental changes may contribute to changes in allelic frequencies in the wild. Given that the foraging gene has similar functions across diverse taxa, the findings described herein suggest that PKG activity may differ across genotypes and prior environmental exposures in a variety of species.

The molecular pathway described herein has been shown to modulate a response to acute hypoxia. The results reveal a series of potential targets that may be of use for therapeutic intervention for pathologies that involve low-oxygen stress, such as stroke, neurodegenerative diseases, and pathologies related to aging. This work also raises the possibility that polymorphisms in genes encoding molecular targets described here contain polymorphisms affecting risk to low-oxygen stress pathologies. At the level of the nervous system, these types of stresses may act to deplete cellular energy, due to hyperactivity during hyperthermia or blockage of cellular metabolism during hypoxia. At the cellular level, the reduction of whole-cell K$^+$ current may be a form of cellular energy conservation that confers tolerance to such stresses.

TABLE 1

| Downstream Agent (from FIG. 3a) | Upstream Agent (from FIG. 3a) | Downstream Target (from FIG. 3a) | Anoxic Coma Onset (FIG. 3b) | | |
|---|---|---|---|---|---|
| | | | Mean (sec) | s.e.m. (sec) | N= |
| 200 mM Dichloroacetate | 10 mM 8-Bromo cGMP | Activates K+ Channels | 269.18 | 4.01 | 14 |
| 200 mM Dichloroacetate | 1 mM KT5823 | Activates K+ Channels | 274.12 | 3.72 | 14 |
| 200 mM Dichloroacetate | 10 mM T0156 | Activates K+ Channels | 280.57 | 5.16 | 12 |
| 10 mM 8-Bromo cGMP | 10 mM T0156 | Activates PKG | 297.36 | 4.56 | 14 |
| 200 mM Dichloroacetate | 1 mM Cantharidin | Activates K+ Channels | 310.20 | 7.00 | 14 |
| CONTROL - DMSO | CONTROL - DMSO | N/A | 346.63 | 2.73 | 65 |
| 1 mM Cantharidin | 10 mM T0156 | Inhibits PP2A | 366.61 | 6.75 | 12 |
| 1 mM KT5823 | 10 mM 8-Bromo cGMP | Inhibits PKG | 391.32 | 4.30 | 12 |
| 1 mM Cantharidin | 10 mM 8-Bromo cGMP | Inhibits PP2A | 403.02 | 6.12 | 12 |
| 1 mM KT5823 | 10 mM T0156 | Inhibits PKG | 410.40 | 4.96 | 14 |
| 1 mM Cantharidin | 1 mM KT5823 | Inhibits PP2A | 410.44 | 5.99 | 12 |

Methods

Fly stocks: Two naturally occurring strains of adult *Drosophila melanogaster* were used in this study; a rover strain homozygous for the for$^R$ allele (high PKG activity), and a sitter strain, homozygous for for$^s$ (low PKG activity). These strains are isogenized natural polymorphisms of the foraging gene, located on the second chromosome. Additionally, the sitter mutant strain for$^{s2}$ which was previously generated in the laboratory was also utilized. This strain has a rover genetic background with a mutation at for leading to PKG activity/transcript levels lower than that observed in sitters. All flies were reared in the same fashion; 12 h light: 12 h dark light cycle with lights on at 0800 h, equal density (approximately 200 flies in a 170 mL plastic culture bottle containing 40 mL of a standard yeast-sucrose-agar medium), and same age (5-9 day old adults at testing time) in an incubator at 25° C. Flies that were used in this study were not exposed to anesthesia for at least 24 hours before trials.

Locomotory Tolerance Assay during Acute Hypoxia: Ten flies (separated into males or females) from each of the three strains (rover [for$^R$], sitter [for$^s$] and for$^{s2}$) were selected and placed in three separate vials with food at least 24 hours before each experiment. At the time of the experiment, flies were emptied into 10 mL empty test vials covered with permeable sponge caps of equivalent thickness, allowing for consistent gas exchange. These test vials were then placed into a 600 mL beaker which was covered with parafilm, creating a closed chamber with an escape hole (1 cm diameter). The parafilm top was punctured with a needle connected to a gas tank (by a plastic hose), through which the inert gas argon was expelled. Pure nitrogen was used, where no significant differences between the use of the two gases was observed. The needle tip was fastened to the bottom of the beaker and inserted into a larger sponge of similar texture to the vial sponge caps to ensure that gas expelled from the needle was dispersed equally throughout the beaker. Also, to ensure that all test vial positions in the beaker received equal gas flow, test vial positions were alternated every trial to reduce variability.

The experiment required exposing the test vials with 10 flies in the container to pure argon gas expelled from the tank at a flow rate of 600 cc/min+/−5%. Time of behavioural failure was recorded by observing the fly undergo a seizure, which was quickly followed by an anoxic coma. A computer program entitled Multi-Arena-Multi-Event-Recorder (MA-MER), was used to record neural failure time for each individual fly. This was accomplished by starting the timer on the program at the initiation of gas flow. The observer would then type "1" if a fly failed in vial 1, "2" for fly failure in vial 2, and "3" for observed failure in vial 3. The program recorded these times of failure for each fly and then computed an average failure time for each vial (each vial was N=1). The averaged failure times represent the N data in the figures, and successfully distinguished failure times among the different strains. Upon failure of all flies, the vials were placed in a freezer at −20° C. to preserve PKG levels at time of behavioural failure. These flies were later subjected to PKG enzyme activity assays to measure PKG enzyme levels. Males and females were tested separately, and no significant differences were found between any of the genotypes or treatments and therefore their data was pooled ($p>0.05$).

Heat shock: Taken from Karunanithi et al. (J Neurosci. 19:4360-4369, 1999), ten flies of a specific strain (for$^R$, for$^s$ and for$^{s2}$) and sex were selected and placed in separate vials. These vials were then placed in a hybridization oven set at 36° C. for 1 hr. The flies were given 30 minutes to recover before being subjected to the anoxic coma assay.

Pharmacological Manipulation: The same behavioural assay described above was employed; however, flies were pre-treated with chemical agents to observe their effects on tolerance to anoxic stress. Unlike previous experiments, the pharmacological behavioural assays were only conducted on the sitter strain. This strain was chosen because of its intermediate tolerance when compared to rovers and the sitter mutant (FIG. 6). Adult sitters were exposed to various drugs predicted to have an effect on targets involved in the PKG pathway. These drugs included (from Sigma Aldrich): 10 mM T0156, a cGMP-specific phosphodiesterase-5 inhibitor, 10 mM 8-Bromo-cGMP, a PKG activator, 1 mM KT5823, a PKG inhibitor, 1 mM Cantharidin, a PP2A inhibitor, and 200 mM DCA, a K$^+$ channel activator. All drugs were solubilized in DMSO, where flies treated with only DMSO were used as a sham controls. A novel assay was developed to administer these drugs to whole adults in vivo through volatilization, since concentrations of the drug at 10-fold concentrations were used in vitro (Dawson-Scully et al., PLoS ONE 2(1): e773, 2007). 10 µL of drug solution was applied to a crushed Kim wipe at the bottom of each test vial. An additional Kim wipe was crushed over top of this to prevent direct contact of the fly on the solution. 10 flies were then placed in the vial which was capped with a semi-permeable buzz-stopper and covered with a cut-out finger of a large latex glove to prevent chemical vapours from escaping in the dark. The flies were subjected to the drug for 1 hr prior to each behavioural assay.

Drug Combinations: Drug combinations were employed to observe the effects of activating and/or inhibiting various participants in the PKG pathway simultaneously to determine downstream and upstream targets. Here, 20 uL of DMSO was used as a control sham, and combinations of two pharmacological treatments were added as two separate 10 uL aliquots. The same drugs and protocol described above were used in this assay. The drug combinations tested were: 10 mM 8-Bromo-cGMP/1 mM KT5823, 10 mM 8-Bromo-cGMP/1 mM Cantharidin, 10 mM 8-Bromo-cGMP/10 mM T0156, 10 mM 8-Bromo-cGMP/200 mM DCA, 1 mM KT5823/1 mM Cantharidin, 1 mM KT5823/10 mM T0156, 1 mM KT5823/200 mM DCA, 1 mM Cantharidin/10 mM T0156, 1 mM Cantharidin/200 mM DCA and 10 mM T0156/200 mM DCA.

PKG enzyme activity assays: PKG enzyme activity assays were conducted according to the procedure outlined in Kaun et al. (J Exp Biol. 210(Pt 20):3547-3558, 2007). Adult *Drosophila* were decapitated and the heads were homogenized in 25 mM 1-1 Tris (pH 7.4), 1 mM 1-1 EDTA, 2 mM 1-1 EGTA, 5 mM 1-1 β-mercaptoethanol, 0.05% Triton X-100 and protease inhibitor solution (Roche Diagnostics). Following microcentrifugation for 5 min, the supernatant was removed and those supernatants containing equal amounts of total protein were examined for PKG enzyme activity. The reaction mixture contained the following substances: 40 mM 1-1 Tris-HCl (pH 7.4), 20 mM 1-1 magnesium acetate, 0.2 mM 1-1 [$\gamma^{32}$P]ATP (500-1000 c.p.m. pmol−1), 113 mg ml−1 heptapeptide (RKRSRAE), (SEQ ID NO:6), (3 mM 1-1 cGMP and a highly specific inhibitor of cAMP-dependent protein kinase. The next step of the procedure involved incubating the reaction mixtures at a temperature of 30° C. for 10 min, followed by ending the reaction by spotting 70 µl of the reaction mixture onto Whatman P-81 filters. To remove any unreacted [$\gamma^{32}$P]ATP, these spots were then soaked with 75 mM 1-1 $H_3PO_4$ for 5 min and washed three times with 75 mM 1-1 $H_3PO_4$. Before quantifying enzyme activity, filters were rinsed with 100% ethanol and air dried. To calculate PKG enzyme activity, counts were taken in a Wallac 1409 Liquid Scintillation Counter using universal scintillation cocktail (ICN). PKG activity was presented in the figures as pmol of $^{32}$P incorporated into the substrate min−1 mg−1 protein.

Statistics: Data were analyzed using One-Way and Two-Way ANOVA followed by a post-hoc Multiple Comparisons test (SNK=Student-Neuman-Keul's test). In cases where normality or equal variance failed, non parametric tests on the ANOVA on ranks were used. Significant differences were established with $p<0.05$, where letters that differed on the graphs signified statistical groupings. In behavioural trials, N=1 represents a trial which consisted of 10 adult flies.

Example 7

Inhibiting the PKG Pathway in Zebrafish

Vertebrate (zebrafish) behaviour is examined during acute anoxia. Whole zebrafish are exposed to anoxic water post-treatment with a PDE5 inhibitor, 8-bromo-GMP, KT5823, and Cantharidin. The time until the animal knocks out during anoxia is monitored. It is expected that drugs which activate the PKG pathway (a PDE5 inhibitor, 8-bromo-GMP) cause increased sensitivity to anoxia causing early failure of behaviour (neural function), while inhibition of this pathway results in neuroprotection and prolonged behaviour when subject to anoxia.

Example 8

Inhibiting the PKG Pathway in Mammals

Neural function in mammals (mouse or rat) is examined pharmacologically during acute anoxia in respiratory brain slices via sodium azide, which chemically induces anoxia. Following administration of the sodium azide, the time until neural failure is monitored. This is done in the presence of a PDE5 inhibitor, 8-bromo-GMP, KT5823, and Cantharidin. It is expected that drugs which activate the PKG pathway (a PDE5 inhibitor, 8-bromo-GMP) cause increased sensitivity to anoxia causing early failure of neural function, while inhibition of this pathway results in neuroprotection and prolonged neural function when subject to anoxia.

Example 9

Inhibiting the PKG Pathway in Mammals

The pharmacological effects of a PDE5 inhibitor, 8-bromo-GMP, KT5823, and Cantharidin during spreading depression are examined in mammals (mouse or rat). It is expected that drugs that activate the PKG pathway (a PDE5 inhibitor, 8-bromo-GMP) cause increased SD-like events causing early failure of neural function, while inhibition of this pathway results in neuroprotection and reduces SD-like events thereby prolonging neural function.

Other Embodiments

Any improvement may be made in part or all of the compositions and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method comprising administering a PKG pathway pharmacological inhibitor selected from the group consisting of: KT5823; (Rp)-8-bromo-PET-cyclic GMPS; (Rp)-8-pCPT-cyclic GMPS, TEA; Rp-8-Br-cGMPS, Na; DT-3; DT-2; amino acid sequence RKRARKE (SEQ ID NO: 5); Okadaic acid; Microcystin; Calyculin; Cantharidin; 4H-8-Bromo-1,2,4-oxadiazolo(3,4-d)benz(b)(1,4)oxazin-1-one; 1H-[1,2,4]Oxadiazolo[4,3-a]quinoxalin-1-one (ODQ); and 6-Anilino-5,8-quinolinequinone to a patient having a medical condition selected from the group consisting of: neuronal damage from spinal cord injury, neuronal damage from stroke, neural anoxia, spreading depression, and migraine, in an amount effective for preventing failure of neural function associated with one or both of neural anoxia and spreading depression in the patient.

2. The method of claim 1, wherein the pharmacological inhibitor is
Rp-8-Br-cGMPS, Na.

3. The method of claim 1, wherein administration of the PKG pathway pharmacological inhibitor mitigates or prevents neural death and damage in the patient.

4. A method of treating a patient experiencing a migraine or susceptible to experiencing a migraine, the method comprising administering a composition comprising a pharmacological inhibitor of the PKG pathway selected from the group consisting of KT5823; (Rp)-8-bromo-PET-cyclic GMPS; (Rp)-8-pCPT-cyclic GMPS, TEA; Rp-8-Br-cGMPS, Na; DT-3; DT-2; amino acid sequence RKRARKE (SEQ ID NO: 5); Okadaic acid; Microcystin; Calyculin; Cantharidin; 4H-8-Bromo-1,2,4-oxadiazolo(3,4-d)benz(b)(1,4)oxazin-1-one; 1H-[1,2,4]Oxadiazolo[4,3-a]quinoxalin-1-one(ODQ); and 6-Anilino-5,8-quinolinequinone to the patient experiencing a migraine associated with one or both of neural anoxia and spreading depression or susceptible to experiencing a migraine associated with one or both of neural anoxia and spreading depression, in an amount effective to treat or prevent the migraine.

5. The method of claim 4, wherein the patient has a predisposition to spreading depression events, and administration of the PKG pathway inhibitor regulates potassium channel conductances.

6. The method of claim 4, wherein the migraine is associated with anoxia.

* * * * *